(12) United States Patent
Fleet et al.

(10) Patent No.: US 6,916,948 B2
(45) Date of Patent: Jul. 12, 2005

(54) BIS(1,3-DIHYDROXY-PROP-2-YL) AMINE AND DERIVATIVES THEREOF IN THE MANUFACTURE OF POLYMERS

(75) Inventors: George W. J. Fleet, Oxford (GB); David Scott, Edinburgh (GB); Malcolm Finn, Sale (GB); Thomas Krülle, Oxford (GB)

(73) Assignee: Isis Innovation Limited, Oxford (GB)

( * ) Notice: Subject to any disclaimer, the term of this patent is extended or adjusted under 35 U.S.C. 154(b) by 303 days.

(21) Appl. No.: 09/949,859

(22) Filed: Sep. 12, 2001

(65) Prior Publication Data

US 2002/0052465 A1 May 2, 2002

Related U.S. Application Data

(63) Continuation of application No. PCT/GB00/00910, filed on Mar. 13, 2000.

(30) Foreign Application Priority Data

Mar. 12, 1999 (GB) ............................................. 9905771

(51) Int. Cl.⁷ ..................... C07C 215/12; C07C 233/78; C08G 83/00; C07H 5/06; C07D 319/06
(52) U.S. Cl. .................... 560/158; 560/169; 544/193.1; 549/370; 549/426; 549/476; 564/51; 564/60; 564/83; 564/224; 564/503; 564/504
(58) Field of Search ................................. 549/370, 426, 549/476; 544/193.1; 560/158, 169; 564/51, 60, 83, 224, 503, 504

(56) References Cited

U.S. PATENT DOCUMENTS

| | | | |
|---|---|---|---|
| 4,237,272 A | 12/1980 | Mochida | ...................... 536/17 |
| 4,476,045 A | 10/1984 | O'Lenick | ...................... 252/545 |
| 4,772,645 A | 9/1988 | Tarbutton | ...................... 523/457 |

FOREIGN PATENT DOCUMENTS

| | | |
|---|---|---|
| EP | 0 025 083 | 3/1981 |
| EP | 0 663 446 | 7/1995 |
| FR | 2 766 187 | 1/1999 |
| WO | WO 96/40104 | 12/1996 |

OTHER PUBLICATIONS

Database CAPLUS on STN, Acc. No. 1999:77554, Bashiardes et al., WO 9903844 (Jan. 28, 1999) (abstract).*
Database CAPLUS on STN, Acc. No. 1997:769193, Gluzman et al., JP 09309882 (Dec. 2, 1997) (abstract).*
Database CAPLUS on STN, Acc. No. 1995:741185, Yamauchi et al., EP 663446 (Jul. 19, 1995) (abstract).*
Database CAPLUS on STN, Acc. No. 1997:151525, Carrell et al., WO 9640104, Dec. 19, 1996 (abstract).*
Database CAPLUS on STN, Acc. No. 1995:674033, Carrell et al., WO 9510272, Apr. 20, 1995 (abstract).*
Scott et al, *Tetrahedron Letters*, 40 (42) : 7581–7584 (1999).
Gross et al, *Adhaesion*, 34 (1–2) : 28–31 (1990) (Abstract).
Tonkyn et al, *J. Appl. Polym. Sci.*, 11 (1) : 145–148 (1967) (Abstract).
Ilczuk et al, *Acta Pol. Pharm.*, 39 (5–6) : 337–343 (1982) (Abstract).
International Search Report.

* cited by examiner

*Primary Examiner*—Brian Davis
(74) *Attorney, Agent, or Firm*—Sughrue Mion, PLLC

(57) ABSTRACT

Derivatives of bis-(1,3-dihydroxy-prop-2-yl)amine are disclosed, together with the use of such derivatives and of bis(1,3-dihydroxy-prop-2-yl)amine itself in the preparation of polymers, in particular dendrimers. Some of the derivatives may be useful as non-ionic surfactants.

27 Claims, No Drawings

BIS(1,3-DIHYDROXY-PROP-2-YL) AMINE AND DERIVATIVES THEREOF IN THE MANUFACTURE OF POLYMERS

This application is a Continuation of PCT/GB00/00910 (published under PCT Article 21(2) in English) filed Mar. 13, 2000. The disclosure of PCT/GB00/00910 is incorporated herein by reference.

The present invention relates to the use of bis(1,3-dihydroxy-prop-2-yl)amine and derivatives thereof, particularly hydroxy-protected derivatives, in the manufacture of polymers.

Conventional polymers have a linear structure comprising a series of residues of the monomers used in preparation of the polymer. In order to modify the chemical and physical properties of the polymer, branching sites may be introduced, e.g. by the use of small quantities of a trifunctional branching agent.

For certain purposes, highly branched polymer structures are desired and where a relatively large quantity of branching agent is used polymer growth proceeds with multiple branching to produce a so-called dendritic structure. In one extreme, symmetrical branching, following growth from a branched core site, can produce the so-called starburst dendrimers. Typically starburst dendrimers may be produced by successive branching at terminal amine nitrogens, e.g. as described by Tomalia et al. in Polymer Journal 17: 117–132 (1985). In such structures each generation, ie. each extension at all preexisting terminal groups, doubles the number of terminal groups.

Dendrimers are highly branched molecules which are able to carry a multiplicity of functional groups at their termini and which as a result have a wide range of applications, e.g. in the production of paints and coatings. Their possession of a multiplicity of terminal functional groups means that dendrimers may be used in fast curing coatings and to achieve enhanced surface adhesion. Dendrimers likewise may be attached to beads or microspheres to modify their properties. Indeed dendritic ligands, as described by Reetz et al. (Angew. Chem. Int. Ed. Engl. 36: 1526 (1997)), possess various attractive properties typically associated with homogeneous catalysts.

We now propose the use of bis-(1,3-dihydroxyprop-2-yl)amine and derivatives thereof to produce branching sites or terminal sites in polymeric structures, in particular dendrimers.

Bis-(1,3-dihydroxyprop-2-yl)amine, with one amine and four hydroxyls, is highly functionalised as compared with many of the structures conventionally used to provide polymer branching and terminus sites, and in particular may be used to produce a higher than usual degree of branching as well as providing a highly hydrophilic intermediate or final structure. Moreover, where the amine nitrogen is appropriately functionalised, dendrimer growth may proceed a generation at a time rather than in half generation stages as in the acrylate:amine Michael addition and subsequent ester amidation described by Tomalia et al. (supra).

Dendritic building blocks may be classified as $AB_n$ compounds, where n represents the degree of branching. For nearly all known dendritic compounds, n=2 or 3. Bis-(1,3-dihydroxyprop-2-yl)amine is a rare example of an $AB_4$ monomer. Use of such a highly branched monomer in the production of dendrimers may allow more units of the required peripheral functionality to be achieved in relatively few generations.

Thus viewed from one aspect the invention provides the use of bis-(1,3-dihydroxyprop-2-yl)amine or a derivative thereof in the preparation of a polymer or a precursor therefor.

For the purposes of this text a polymer may be taken to mean a structure containing at least two repeated structural motifs linked together directly or indirectly, e.g. a structure -M-M-M-M-, -M-A-M-A-M-,

where M is the repeated motif and A is a bridging unit. Preferably, the polymers will contain at least 3, and more preferably at least 6 such repeated motifs. Preferably, the polymer is a dendrimer.

The bis-(1,3-dihydroxyprop-2-yl)amine or derivative thereof used according to the invention is conveniently a compound of formula I

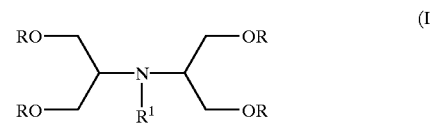

where each R, which may be the same or different is a hydrogen atom or a hydroxy protecting group, preferably two R groups together representing a $C_{1-6}$ alkylene or oxo-alkylene group serving to produce a 6 to 8 membered 1,5-bis-oxa-cycloalkan-3-yl ring; and $R^1$ is a hydrogen atom, a $C_{1-50}$ (preferably $C_{1-6}$) alkyl group optionally substituted by amino, hydroxy, halo, alkoxy, oxo, aryl, heteroaryl or carboxy groups, or by a 5–6 membered hydroxylated- oxa- or aza-cycloalkyl group, or $R^1$ is a $C_{4-8}$ cycloalkyl group, an amine protecting group, a substituted phosphorus or sulphur atom, a 5- or 6-membered hydroxy-oxa or aza- cycloalkyl group, an optionally protected 1,3-bis-oxacycloalkan-5-yl group, an amino group, or an aryl or heteroaryl group, with the provisos that when each R group is hydrogen, then $R^1$ is not —$CH_2CH_2OH$, and when $R^1$ is n-propyl, t-butyl or phenyl, R is not 4-methylphenyl.

Examples of suitable hydroxy protecting (R) groups and amine protecting groups are well known from the literature. See for example Greene, "Protective groups in organic synthesis", Wiley-Interscience, New York, 1981, and McOmie, "Protective groups in organic chemistry", Plenum, 1973.

Suitable hydroxy protecting groups include alkylcarbonyl groups, for example acetyl, and trialkysilyl groups, for example t-butyldimethylsilyl. Particularly preferred protecting groups include N-substituted aminocarbonyl groups, and bridging methylene and ethylene groups optionally substituted by oxo or $C_{1-3}$ alkyl or aryl groups, e.g. where the 1,3-bishydroxyprop-2-yl group is presented as

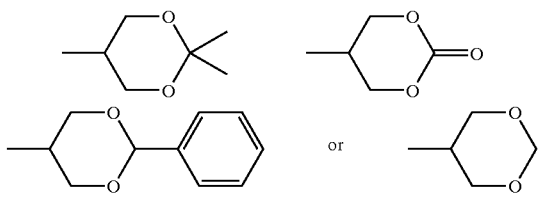

The groups $R^1$ on the amine nitrogen may for example be amine protecting groups or groups which activate the amine for conjugation to other chemical species, e.g.

aminoalkylcarbonyl, alkoxycarbonylalkyl, arylaminocarbonyl, arylcarbonyl, halocarbonyl, heteroarylcarbonyl, heteroaryl, hydroxyalkyl, carboxyalkyl, carboxyalkylcarbonyl, arylalkyl, aryl, amino, aminoalkyl, hydroxyalkyl, cycloalkyl, sulphonyl, phosphoryl, oxacycloalkyl, oxacycloalkyl-alkyl, oxacycloalkylcarbonyl, azacycloalkyl, azacycloalkyl-alkyl or azacycloalkylcarbonyl groups.

In one preferred embodiment $R^1$ is an optionally hydroxy-protected 1,3-dihydroxy-prop-2-yl group, ie. a group —CH(CH$_2$OR)$_2$.

Many of the compounds of formula I are novel compounds and thus viewed from a further aspect the invention provides a compound of formula I wherein at least two R groups, and preferably four R groups, are other than hydrogen. A particularly preferred set of compounds of formula I are the compounds of formula II

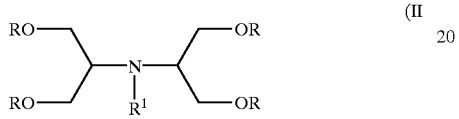

(II)

wherein each R is a hydrogen atom, a $C_{1-6}$ alkyl group, an alkylcarbonyl group or an aminocarbonyl group;

or two R groups together represent a bridging group $C(R^2)_2$ wherein each $R^2$ is a hydrogen atom, a $C_{1-6}$ alkyl group or an aryl group or both $R^2$ together represent an oxygen atom;

and $R^1$ is a hydrogen atom, a $C_{1-50}$ (preferably $C_{1-6}$) alkyl group optionally substituted by amino, hydroxy, halo, alkoxy, oxo, aryl, heteroaryl or carboxy groups, or $R^1$ is an aminocarbonyl group, an alkylcarbonyl group, a monosaccharide optionally attached via a methylene or carbonyl group, an optionally protected 1,3-bishydroxyprop-2-yl group, a chlorocarbonyl group, or a group $X(N(CH(CH_2OR)_2)_2)_n$ where X is a bond or a 1 to 50 backbone atom linking group, and n is an integer having a value of from 1 to 10, preferably 1, 2, 3, 4, 5 or 6, with the provisos that (a) where $R^1$ is hydrogen or an optionally protected 1,3-bishydroxyprop-2-yl group at least two R groups are other than hydrogen; and (b) when $R^1$ is hydrogen and two R groups are hydrogen, the other two R groups are not methyl; and (c) when X denotes 4-((1,3-bishydroxyprop-2-yl)amino) phenyl, then at least one R group is other than hydrogen; and (d) when each R is hydrogen, $R^1$ is not $CH_2CH_2OH$.

In the compounds of the invention, alkyl and alkylene moieties preferably are linear $C_{1-50}$, e.g. $C_{2-25}$ moieties, $C_{1-6}$ linear or branched moieties, or $C_{4-10}$ mono or polycyclic alkyl moieties optionally substituted by or attached via $C_{1-6}$ linear or branched alkyl moieties. Cycloalkyl groups preferably contain 4 to 10 ring atoms, especially preferably 5, 6 or 7 ring atoms. Aryl groups may be carbocyclic or heterocyclic and conveniently contain 1, 2 or 3 rings and a total of 5 to 14 ring atoms. In any heterocyclic ring, there will conveniently be 1, 2 or 3 ring heteroatoms, e.g. selected from O, N and S. Saccharide rings will generally be five or six-membered saturated rings containing a ring oxygen or nitrogen and substituted at preferably at least 2 ring carbons by hydroxyl groups.

Thus by way of example the following are preferred examples of compounds of formula II

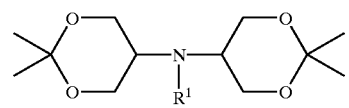

where $R^1$ is H, $CH_2COOCH_3$, $H_2NCH_2CO$, PhCO, PhCH$_2$ (where Ph is an optionally substituted, e.g. NO$_2$, NCO or NH$_2$ substituted, phenyl group), ClCO, imidazolylcarbonyl (e.g. imidazol-1-ylcarbonyl), HOOC(CH$_2$)$_m$, HO(CH$_2$)$_m$, HOOC(CH$_2$)$_m$CO, H$_2$N(CH$_2$)$_m$ (where m is 1 to 50, especially 1 to 6), 2-Ph-1,3-bis-oxa-cyclohexan-5-yl or 1,3-dihydroxyprop-2-yl or is a group $X(N(CH(CH_2OR)_2)_2)_n$ where X serves to link together two or more, e.g. 2, 3, 4, 5 or 6

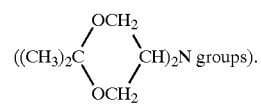

$((CH_3)_2C \begin{smallmatrix} OCH_2 \\ OCH_2 \end{smallmatrix} CH)_2N$ groups).

Other preferred compounds of formula II include compounds wherein R is hydrogen, and $R^1$ is a $C_{1-20}$ alkyl group, preferably a $C_6$–$C_{16}$ alkyl group and more preferably a $C_8$–$C_{12}$ alkyl group, an aminocarbonyl group of formula $R^{10}R^{11}NCO$ or an alkylcarbonyl group of formula $R^{11}CO$, wherein $R^{10}$ denotes hydrogen or $R^{11}$, and $R^{11}$ denotes a $C_{1-20}$ alkyl group, preferably a $C_6$–$C_{16}$ alkyl group and more preferably a $C_8$–$C_{12}$ alkyl group. Examples of such compounds include:

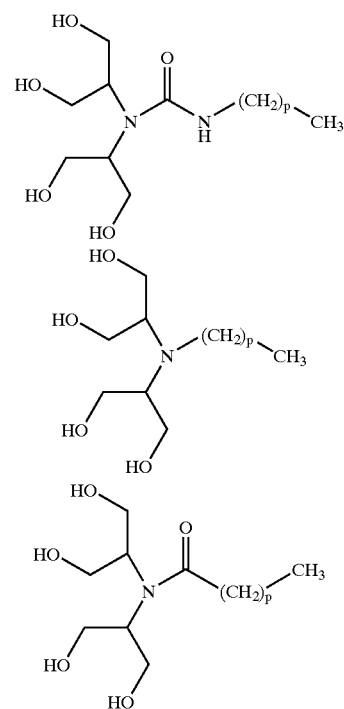

p = 7–11

Such compounds may have utility as non-ionic surfactants or detergents.

Other preferred compounds of formula I or formula II are compounds wherein R denotes H or two R groups together represent a bridging group $C(R^2)_2$ wherein each $R^2$ is a hydrogen atom, a $C_{1-6}$ alkyl group or an aryl group or both $R^2$ together represent an oxygen atom, and $R^1$ denotes an amino-substituted alkyl group. Preferably the alkyl group is an n-alkyl group, for example a $C_1$–$C_6$ n-alkyl group such as ethyl, n-propyl or n-butyl. Preferably the amino group is attached to the carbon atom furthest away from the N atom of the bis-(1,3-dihydroxyprop-2-yl)amino group. Preferred aminoalkyl groups include $CH_2CH_2NH_2$, $CH_2CH_2CH_2NH_2$ and $CH_2CH_2CH_2CH_2NH_2$.

Examples of compounds of formula I or II where $R^1$ comprises a saccharide include:

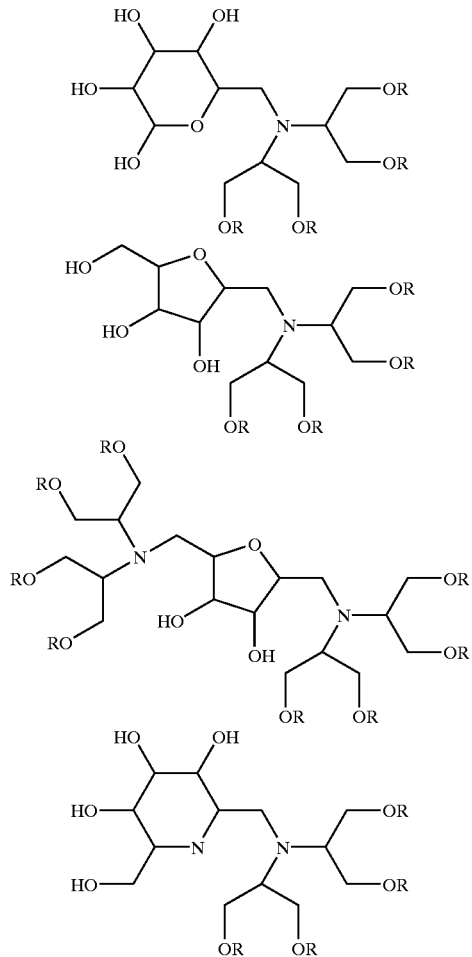

Where $R^1$ is a group $X(N(CH(CH_2OR)_2)_2)_n$, the compound of formula I may be directly useful or it may be used as a core site, bridging site or terminal site in a larger polymer. Examples of such compounds of formula I include

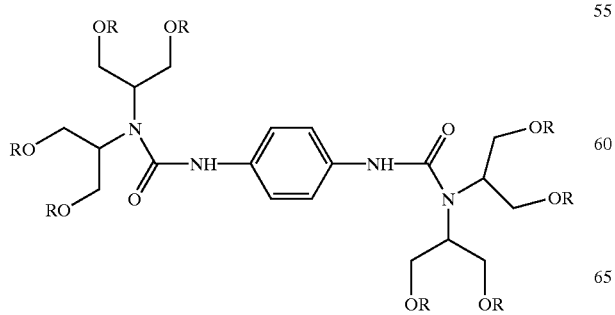

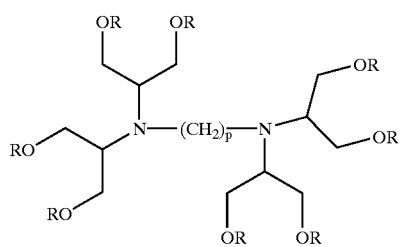

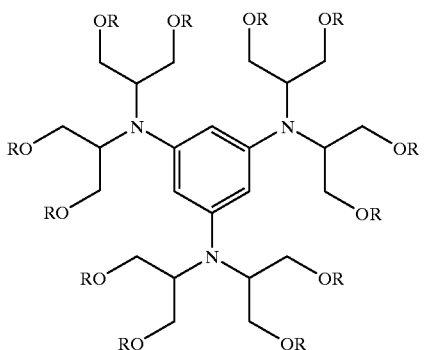

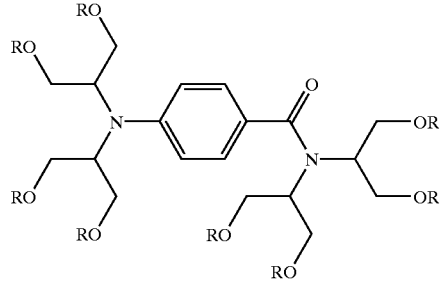

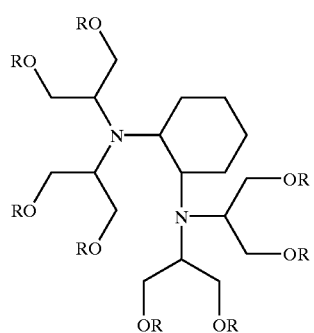

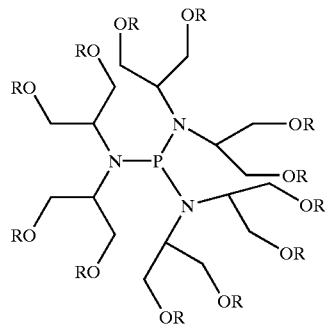

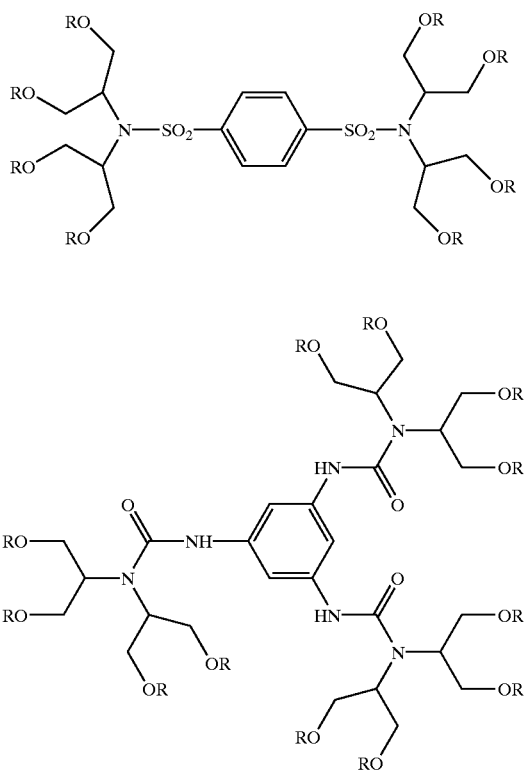
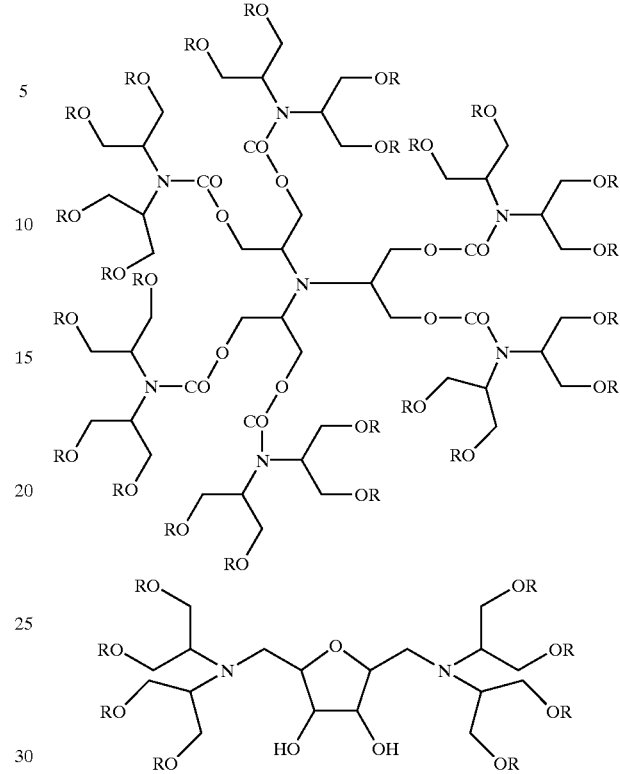
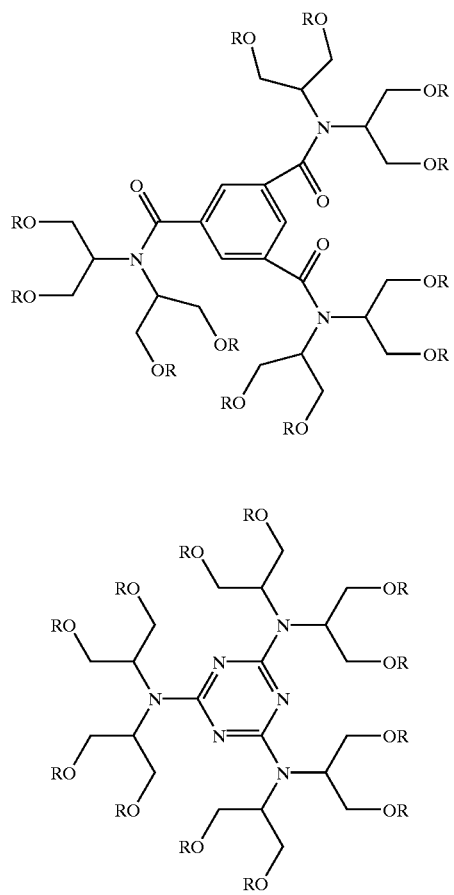

where each R is H or a hydroxyl protecting group, e.g. with two R groups together forming a 1,3-dioxa-cyclohex-5-yl group.

The compounds of the invention in which R, $R^1$ or Z (which is defined below) comprises a saccharide moiety may have utility in affinity chromatography, for example for use in the purification of enzymes. These compounds could be attached to a column or onto the surface of beads or mircospheres to provide a plurality of recognition sites.

The compounds of the invention in which R, $R^1$ or Z (which is defined below) comprises a saccharide moiety may moreover have direct utility, e.g. in therapeutic treatment. Several such compounds are analogous to the known imino sugars, a general family of glycosidase inhibitors which additionally inhibit other sugar metabolizing enzymes. Accordingly such compounds have potential applications as diverse as the inhibition of glycosyl transferases, and the inhibition of the biosynthesis of microorganism cell walls, e.g. in treatment to combat mycobacterial infection, and in the treatment of tuberculosis, leprosy and other related infections, and in the treatment of late-onset diabetes. Likewise such compounds may be used, for example bound to solid substrates, such as polymer microspheres, or proteins, as materials for use in generating antibodies to the saccharide units they present.

Thus viewed from a further aspect the invention provides the use of a compound of formula I or III (as defined below) in which at least one R, $R^1$ or Z group comprises a hydroxylated oxa- or azacycloalkyl moiety in therapy or prophylaxis. Moreover viewed from a still further aspect the invention provides a pharmaceutical composition comprising a compound of formula I or III in which at least one R, $R^1$ or Z group comprises a hydroxylated oxa- or azacycloalkyl moiety together with at least one pharmaceutical diluent or excipient.

Such compositions may be in any suitable administration form, e.g. solutions, suspensions, syrups, aerosols, patches, powders, capsules, tablets or suppositories. Solutions or other presentation forms in sterile aqueous vehicles or tablets comprising conventional tableting aids, e.g. binders, bulking agents, and lubricants may be preferred.

The compounds of and used according to the invention may be prepared from the known compound bis-(1,3-dihydroxy-prop-2-yl)amine (3). This compound itself may be prepared by the reductive amination of dihydroxyacetone. The diacetonide compound of formula II in which $R^1$ is hydrogen and each of the hydroxyls is protected in a 1,3-dioxa-cyclohex-5-yl group may be prepared from bis-(1,3-dihydroxyprop-2-yl)amine (3) by reaction with acetone:

groups in the bis(1,3-dihydroxyprop-2-yl)amine product, and (iii) optionally reacting the secondary amine product with a reagent serving to transform said product into a tertiary amine.

In step (i) of this process, reductive amination may typically be effected using a cyanoborohydride reducing agent, or using other borohydride reducing agents such as sodium triacetoxyborohydride (see for example Abdel Magid et al. J. Org. Chem. 61: 3849–3862 (1996)), or for example using catalysed hydrogenation, e.g. using palladium, rhodium, nickel, ruthenium or platinum based hydrogenation catalysts, for example in a solvent system comprising one or more of water, dioxan, ethyl acetate, $C_{1-4}$ alkanols (e.g. methanol, ethanol, etc), or acetic acid. Reductive amination may also be carried out using ammonium formate in the presence of palladium.

Viewed from a further aspect the invention also provides a polymer comprising at least one 1,3-dihydroxyprop-2-yl or hydroxyl protected 1,3-dihydroxyprop-2-yl substituted amino function, preferably at least one bis(1,3-

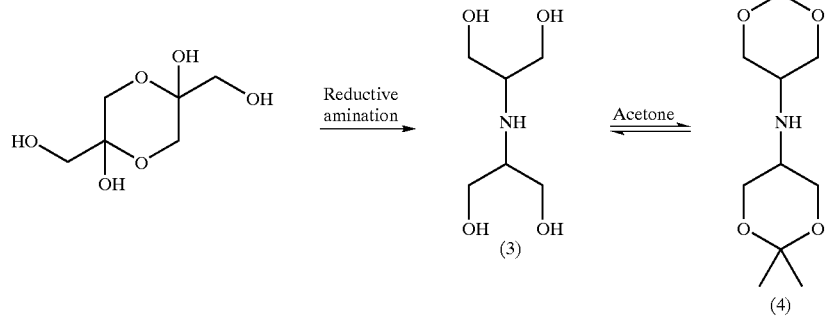

dihydroxyprop-2-yl) or hydroxy protected bis(1,3-dihydroxyprop-2-yl) substituted amino function.

The diacetonide (4) is used herein as a representative compound of formula I and II, but those skilled in the art will appreciate that depending on the reaction conditions to be employed, other hydroxyl protecting groups may be used in place of the acetonide groups. However, acetonide is a preferred protecting group.

The diacetonide (4) may be reacted with appropriate reagents to introduce non-hydrogen $R^1$ groups, e.g. by nucleophilic displacement of a leaving group in the reagent by the nitrogen atom of (4). Examples include reaction with a haloalkyl or haloalkenyl group to introduce an alkyl or alkenyl group; reaction with an isocyanate to introduce an aminocarbonyl group; reaction with an N-protected α-amino acid to introduce an aminoacetyl group; reaction with a haloacetate, e.g. to introduce an alkoxycarbonylmethyl group; reaction with an acyl chloride to introduce an acyl group; or reaction with a bis isocyanate to couple two bis(1,3-dihydroxyprop-2-yl)amines together via urea bonds. In addition, the diacetonide (4) can be used as the amine in a reductive amination of an aldehyde, eg by reaction with an aldehydo-acid to introduce a carboxyl group attached to the nitrogen atom in (4) via a spacer group.

The unprotected compound (3) may also be used directly as the amine in a reductive amination reaction.

This process for producing protected and unprotected bis(1,3-dihydroxyprop-2-yl)amines is novel and forms a further aspect of the present invention. Viewed from this aspect the invention provides a process for preparing a secondary amine comprising (i) reductive amination of dihydroxyacetone, (ii) optionally protecting hydroxyl Such polymers, and compounds of Formula I and II, could be of use as cross linking agents in, for example, paints, coatings, varnishes, gelling agents, emulsifying agents or adhesives. The use of such polymers could provide a mechanism for controlling the rates of drying and/or the toughness of coatings by varying the ratio of NH to OH groups and/or the amount of branching in the polymers. The degree of cross linking in the coatings would be dependent in part on the ratio of the NH to OH groups and on the degree of branching and functionality of the polymers. Such polymers and compounds may also be useful in non-ionic detergents, as surfactants and in controlling the formation of ice crystals in foods, gas hydrates etc.

Viewed from a yet further aspect the invention comprises a process for the preparation of a polymer which process comprises using as a monomer, as a branching agent or as a chain termination agent a 1,3-dihydroxyprop-2-yl or hydroxyl protected 1,3-dihydroxyprop-2-yl substituted amine compound, preferably a bis(1,3-dihydroxyprop-2-yl) or hydroxy protected bis(1,3-dihydroxyprop-2-yl) substituted amine compound.

The 1,3-dihydroxyprop-2-yl-amine structure may also be used for the generation of polymeric structures or modified sugars when the amine nitrogen carries only one bishydroxypropyl group or where two or more such monofunctionalized amine nitrogens are separated within a molecular structure, e.g. attached directly or indirectly to different ring atoms of a mono or polycyclic ring system. Thus viewed from a further aspect the invention provides the use of a 1,3-dihydroxy-prop-2-ylamine or a derivative thereof in the preparation of a polymer or a precursor therefor. The 1,3-dihydroxyprop-2-ylamine used in this regard is conveniently a compound of formula III

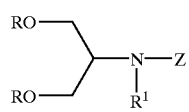
(III)

where R and $R^1$ are as hereinbefore defined and Z is a hydrogen atom, an alkanoic acid, or a mono- or bicyclic aryl group or $R^1$ and Z together with the intervening nitrogen represent an optionally substituted mono or polycyclic saturated or unsaturated heterocyclic group.

The compounds of formula III may be prepared by N-alkylation of a primary or secondary amine with an alkylating agent serving to introduce a 1,3-dihydroxypropyl or protected 1,3-dihydroxypropyl group followed if required by deprotection.

Thus for example the compounds of formula III may be modified amino sugars from which novel polysaccharides may be constructed. Examples of such compounds include compounds of formula V or VII

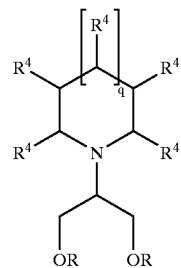
(V)

(where q is 0 or 1, each $R^4$ which may be the same or different is hydrogen, hydroxyl or optionally hydroxy or amino substituted $C_{1-4}$ alkyl, e.g. hydroxymethyl with the proviso that at least one $R^4$ is hydroxy) or

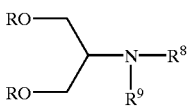
(VII)

where $R^8$ is a 5- or 6-ring membered oxa or aza cycloalkyl group optionally attached via a $C_{1-2}$ alkylene group and substituted by one or more hydroxy or hydroxy $C_{1-4}$ alkyl (e.g. hydroxymethyl) groups and $R^9$ is hydrogen, hydroxy $C_{1-6}$ alkyl or $C_{2-5}$ acyl (e.g. acetyl).

Compounds of formulae V and VII are new and form further aspects of the invention.

Examples of amino sugars of formula V include compounds of formulae

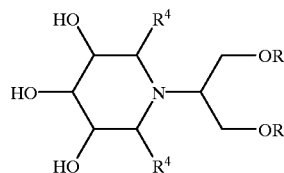

(where each $R^4$ is hydrogen, hydroxymethyl, methyl or amino-methyl (e.g. bis-(1,3-dihydroxyprop-2-yl) aminomethyl), preferably with at least one $R^4$ representing hydroxymethyl) and

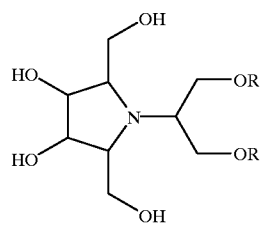

Examples of the modified sugars of formula VII include

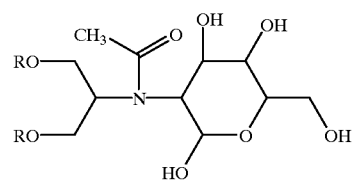

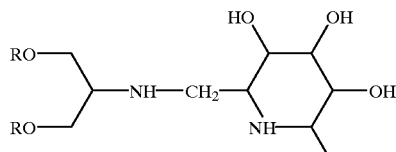

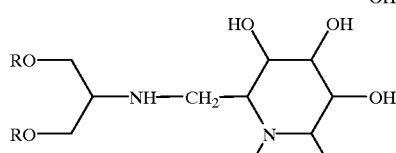

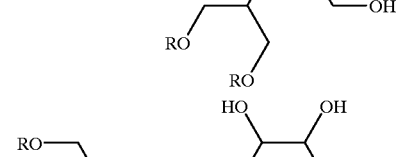

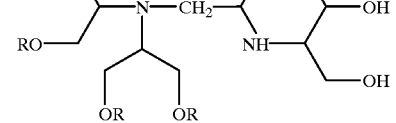

Such amino sugars may be used comparably to natural sugars in the production of polymers, e.g. polysaccharides optionally incorporating natural saccharide.

In the preparation of polymers using such 1,3-dihydroxyprop-2-yl amines, either or both the mono-1,3-dihydroxyprop-2-yl amines and the bis(1,3-dihydroxyprop-2-yl) amines according to the invention may be used and indeed other monomers in which an amine nitrogen is modified to carry a hydroxy $C_{1-4}$ alkyl group (e.g.

2-hydroxyethyl, hydroxymethyl, 2,3-dihydroxypropyl, 3-hydroxypropyl, 2-hydroxypropyl and 2,3,4-trihydroxybutyl) may also be used.

The production of polymeric and non-polymeric compounds according to the invention is illustrated further by the following reaction schemes:

Thus a compound of formula I wherein $R^1$ denotes hydrogen and in which the hydroxyl groups are protected by suitable protecting groups could be elaborated by a large number of reactions based on the nucleophilic nitrogen. Many such reactions are known in the art. In many of the Schemes below the diacetonide (4) is used as an example of a suitably protected compound of formula I but any hydroxyl-protecting groups known in the art which are stable under the reaction conditions to be employed could equally be used. Scheme 1 illustrates the formation of a solubilising end group for peptide synthesis in which otherwise insoluble peptides could readily have a hydroxylic group introduced at either the N-terminal or C-terminal end.

of a C-terminal group in a peptide sequence to give (8). In either case, a final deprotection step would liberate the hydroxyl groups. A similar sequence with any optically active amino acid component would allow a homochiral hydroxylic group to be introduced.

Compounds such as (5) could be further elaborated by liberation, e.g. by base hydrolysis, and reaction of the acid functionality. Alternatively, the ester functionality could be reduced to the corresponding alcohol, e.g. using $LiAlBH_4$, and the alcohol fucntionality reacted further. In a similar manner, removal of the N-protecting group in compound (7) will liberate an amino functionality for further reaction. Such methodology allows the introduction on functionalised linker groups into the compounds of formula I wherein $R^1$ denotes H.

A wide range of groups could be introduced onto the nitrogen atom of a compound of formula I wherein $R^1$ denotes hydrogen by nucleophilic displacement of a leaving group by the nitrogen atom. Suitable leaving groups would

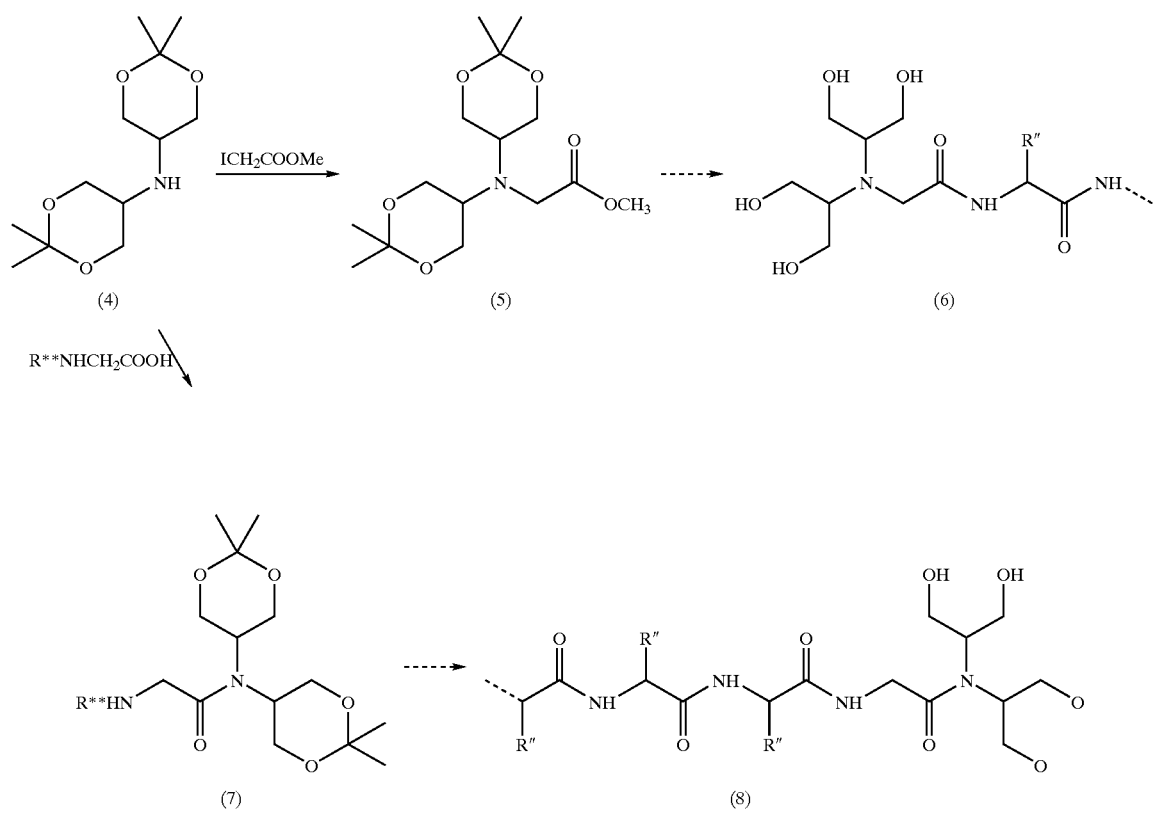

Scheme 1
Alkylation and acylation of (4) exemplified by formation of solubilising peptide units R** denotes a N-protecting group, for example CBZ (carbobenzyloxy) and each R″ denotes an amino acid side chain Thus reaction of (4) with iodoacetate would give (5) which on base hydrolysis of the ester group could be used to introduce N-terminal groups to a peptide sequence to give (6); alternatively coupling of N-protected glycine with (4) would provide an intermediate (7) suitable for incorporation include sulfonate esters or halides. Thus, reaction of compound (4) with an alkyl halide would result in alkylation on the nitrogen atom. Reaction of compound (4) with an alkenyl halide results in alkenylation of the nitrogen atom, as illustrated in Scheme 2.

Scheme 2
Alkenylation of (4) exemplified by formation of linker (12)

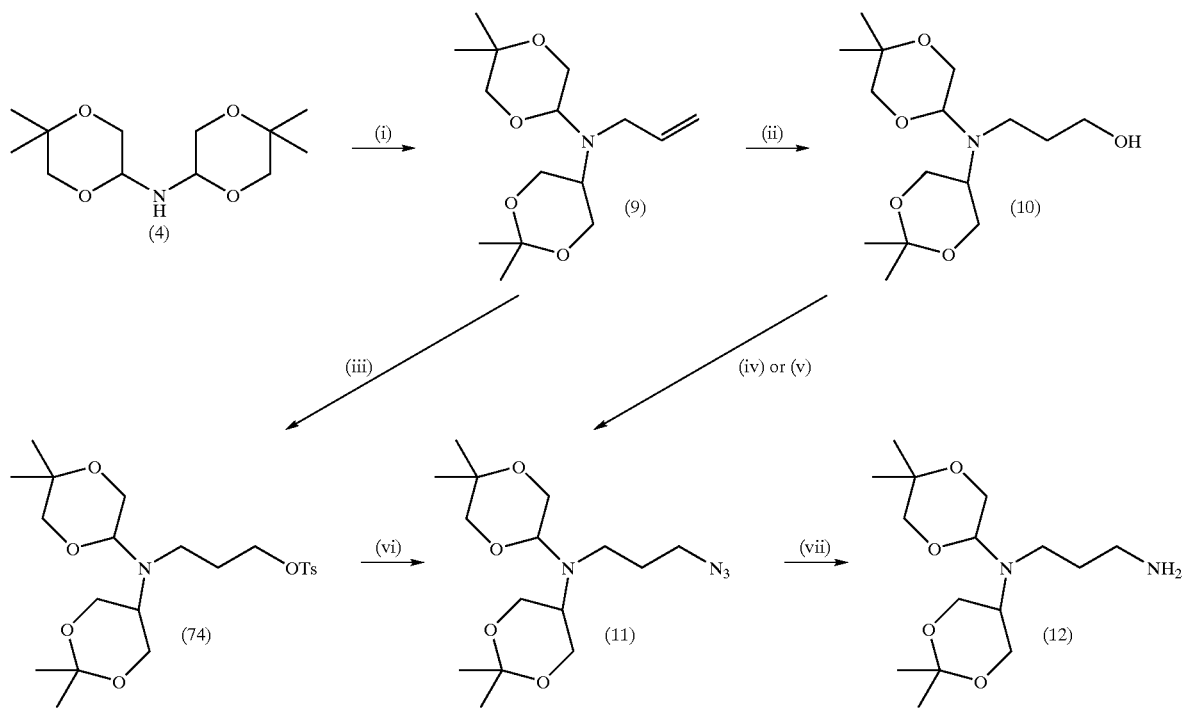

(i) CH₂=CHCH₂I, DMF, K₂CO₃, 70° C. (ii) a) 9-BBN, THF b) H₂O₂, NaOH, 60° C. (iii) Ts₂O, py, 3Å sieves (iv) (PhO)₂PON₃, DBU, DMF, 60° C. (v) MsCl, EtNⁱPr₂, DMF, 0° C. then NaN₃, RT (vi) NaN₃, DMF (vii) H₂, Pd black, EtOAc The alkenyl group thus introduced into compound (9) may be further elaborated using conventional synthetic methodologies. Thus hydroboration of (9) gives the alcohol (10) which may be converted into the corresponding azide (11) via conversion of the OH group into a leaving group followed by displacement by azide. Subsequent reduction of the azide (11) yields amine (12).

Acylation of (4) with an acid chloride leads to formation of an amide linkage. For example, reaction of (4) with 4-nitrobenzyl chloride, followed by reduction of the nitro group to an amine group leads to compound (22) in Scheme 5 below. A typical procedure for the acylation of (4) with 4-nitrobenzoyl chloride (13) is given in Scheme 3 in the preparation of the nitrobenzoic acid amide (14).

Scheme 3
Acylation using p-nitrobenzoyl chloride

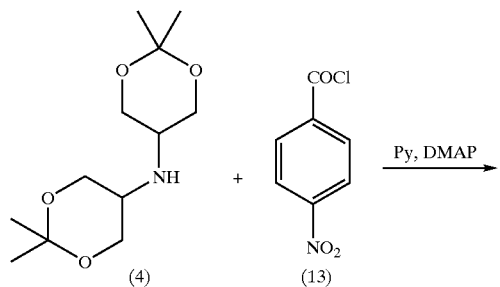

-continued

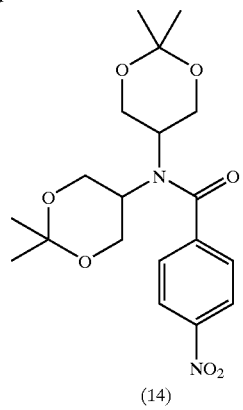

(14)

Compound (14) can be further elaborated by reduction of the nitro group to an amine group (compound (22) in Scheme 5) by for example catalytic hydrogenation. Synthetic chemistry can then be carried out on the amine group, for example via formation of an isocyanate group on reaction with a phosgene equivalent.

There are many other ways the nucleophile (4) could be introduced into molecules including dendrimers. Thus, reaction with an isocyanate such as (15) leads to the formation of ureas as shown for example in Scheme 4.

Scheme 4
Formation of Ureas

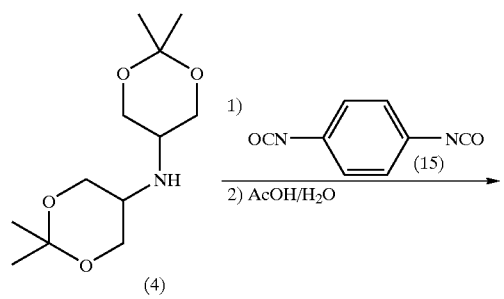

(4)

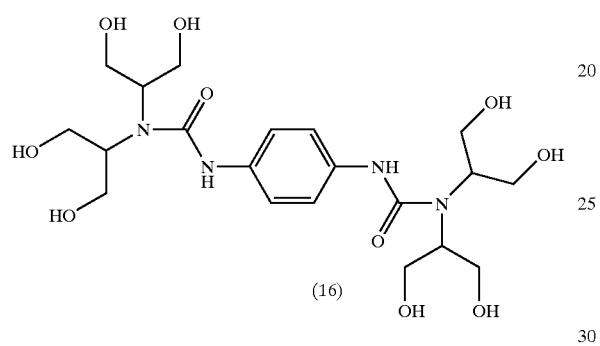

(16)

Ureas such as (16) have potential utility as non-ionic surfactants.

An alternative method for the synthesis of ureas would be the reaction of (4) with phosgene (or a phosgene equivalent) followed by loss of HCl to form an isocyanate, followed by reaction of the isocyanate with a second amine.

Using the above methodology, the original diacetonide (4) could be modified to produce a wide range of alternative linkers, some of which are illustrated in Scheme 5.

Scheme 5
Examples of alternative linkers derived from (4)

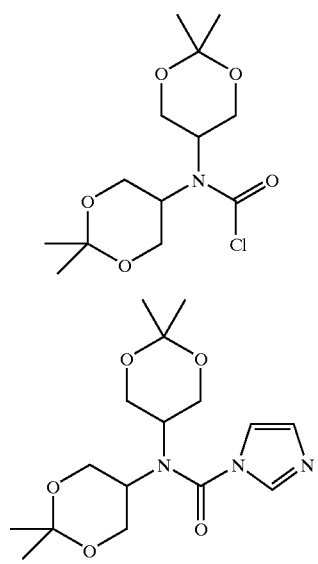

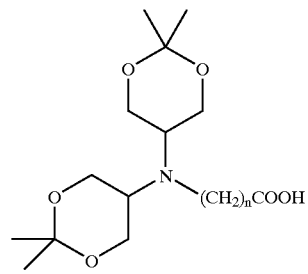

(19)

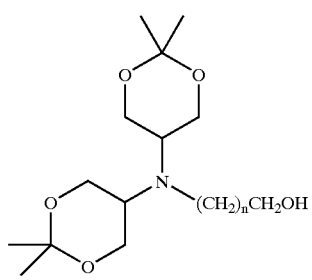

(20)

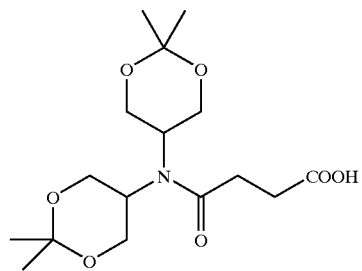

(21)

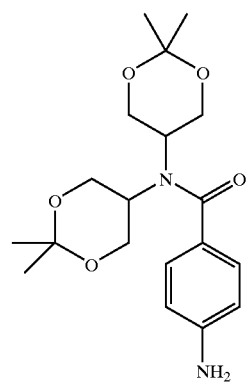

(22)

-continued

(23)
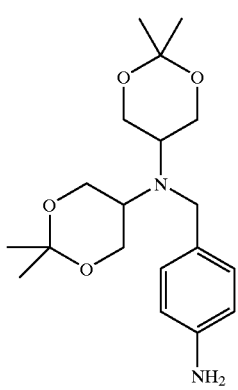

(24)
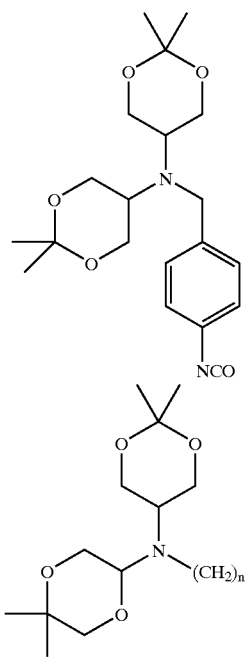

(12) n = 3
(39) n = 2

A very wide range of divergent dendritic monomers could be derived from (4). The diacetonide (4) is a relatively crowded amine and the links from it are most likely made by nucleophilic attack of the nitrogen. Treatment with phosgene or an equivalent would form the carbamoyl chloride (17) which could itself be attacked by nucleophiles to make a bond to the carbonyl group. Alternatively, a similar series of reactions could be derived from the imidazolide (18), e.g. with activation by methylation of the imidazole fragment. There are also a large number of alternative linkers with a spacer between the nitrogen of (4) and the functional group which would allow dendrimers to be formed by less hindered units. These are illustrated by the linked amino acid (19) and alcohol (20) which are formed via alkylation of (4); the corresponding amides as exemplified by (21) can also be formed by treatment of (4) with acid anhydrides. Similarly, aromatic rings could also be incorporated into linkers to provide monomers such as (22), (23) and (24) which would allow mixed functional groups in the dendrimer and polymeric units. Linked amines such as (12) and (39) provide monomers which still contain an amine functionality for further elaboration, but one which is much more reactive than the amine group in (4) itself as it is less sterically hindered.

Additionally all the above structures and modification could be used with other cyclic and non-cyclic protecting groups than the acetonide; some are illustrated in Scheme 6. Other ketals such as the formaldehyde acetal (25), and the generalised acetal structure (26)—exemplified specifically be the benzylidene derivative (27) and all the other stereoisomers thereof, ester (28) and ether (29) protecting groups. For example, treatment of (3) with acetic anhydride in pyridine leads to formation of the tetracetate ester (33) as the major product. In particular the cyclic carbonate (30) and its derivatives on reaction with a suitable amine may allow the formation of carbamates such as (31) simultaneously providing a free OH group and allowing non-symmetrical branches as illustrated in the formation of (31).

Scheme 6
Examples of alternative 1,3-dihydroxypropyl Protecting groups (4)
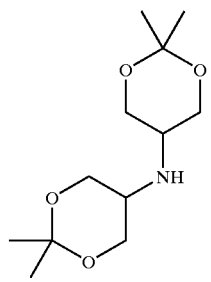

(25)
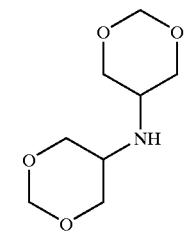

(26)
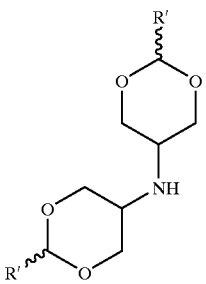

(27)
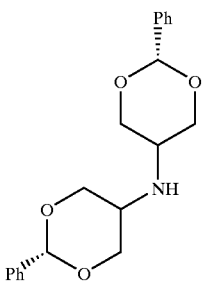

(28)

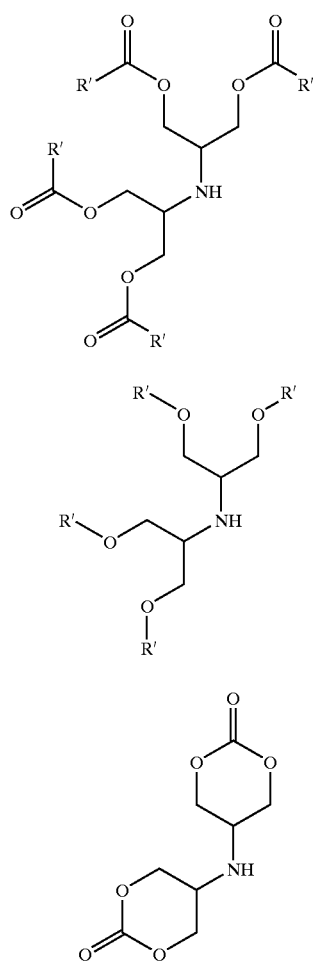

(29)

(30)

(31)

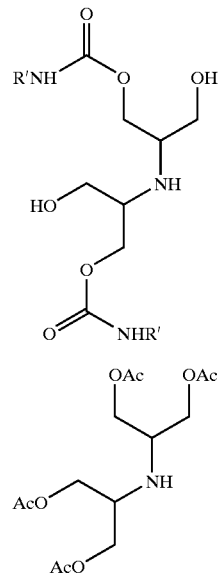

(32)

Further reductive amination [Scheme 7] of either (3) or the diacetonide (4) with dihydroxyacetone itself or protected equivalents thereof such as the benzylidene ketone (37) would allow access to extremely highly branched sources of highly functionalised primary alcohols. Thus reductive amination of the unprotected dimer (3) with dihydroxyacetone would provide (33) with six unprotected primary alcohols whereas reductive amination with (37) would provide a highly branched unit (34) with four unprotected primary alcohol functionalities. Similarly reductive amination of the acetonide (4) with dihydroxyacetone would form the diacetonide (35) with two free primary OH groups while reductive amination with (37) would form the fully protected (36). Such intermediates could be combined with derivatives of the diacetonide (4) to give rise to a wide range of dendritic structures.

Scheme 7
Further reductive amination using (3) & (4) to a highly divergent unit

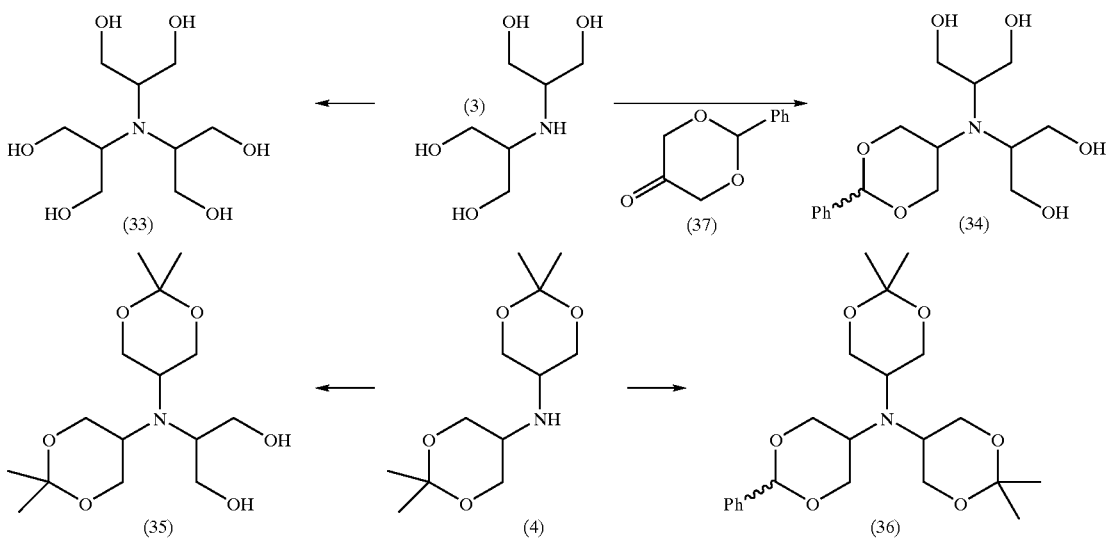

Reductive amination may also be used to introduce optionally substituted alkyl groups onto the N atom in either (3) or (4). Thus, Scheme 8 illustrates two alternative routes to tertiary amine (38), both of which involve reductive amination of aldehyde $Me(CH_2)_2CHO$. Use of aldehydes of different chain length leads to the introduction of alkyl groups of different lengths.

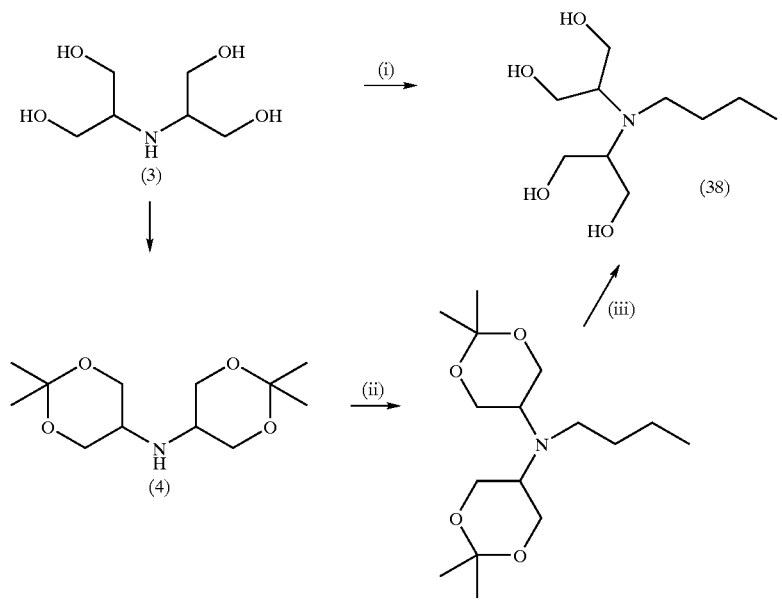

Scheme 8
Reductive amination of aldehydes by (3) and (4)

(i) $Me(CH_2)_2CHO$, $H_2$, Pd black, $H_2O$
(ii) $Me(CH_2)_2CHO$, $NaBH(OAc)_3$, DCE
(iii) $TFA:H_2O$ If a functionalised aldehyde is used in the reductive amination, further functional groups may be introduced into diacetonide (4). Schemes 9 to 12 illustrate various reductive aminations which serve to introduce additional functional groups into (4). These functional groups can then be elaborated using conventional synthetic techniques. For example, reductive amination of (4) using $ClCH_2CHO$ as the aldehyde provides an alternative route to chloride (40) and amine (39) rather than via ester (5) (Scheme 9). Reductive amination with protected aminoaldehyde (43) provides a yet further alternative route to amine (39) (Scheme 9).

Scheme 9
Reductive amination of functionalised aldehydes

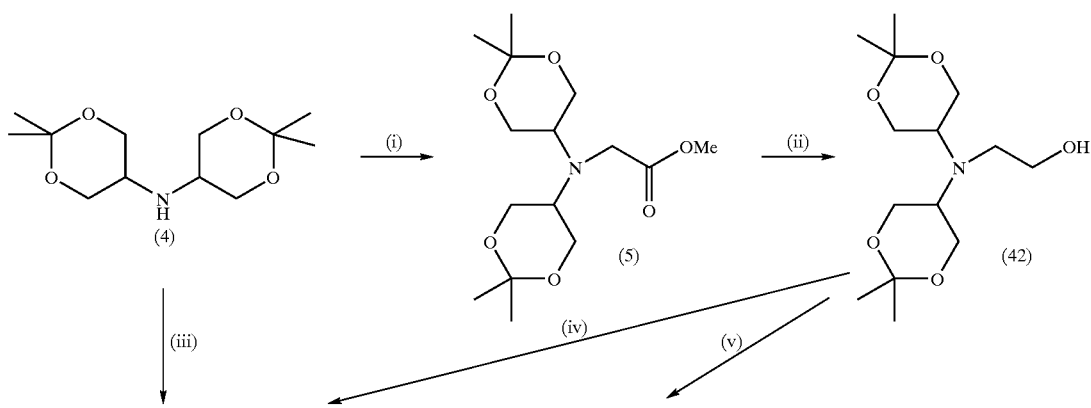

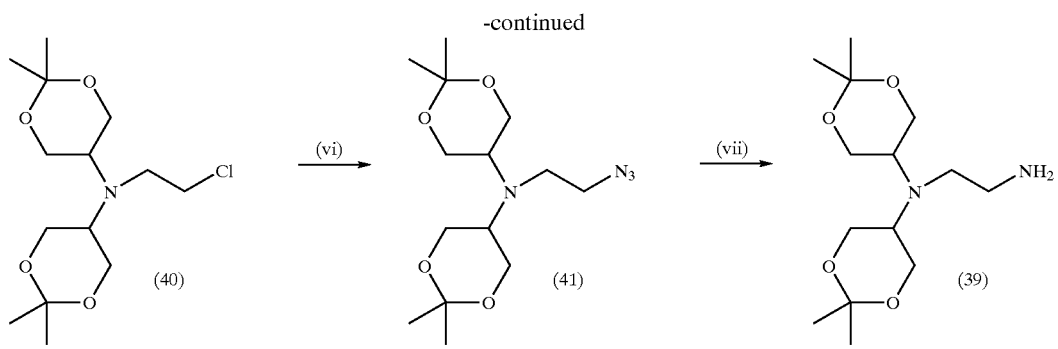

(i) BrCH$_2$CO$_2$Me, toluene, EtN$^i$Pr$_2$, cat. Bu$_4$NI, 110° C.
(ii) LiBH$_4$, THF
(iii) ClCH$_2$CHO, NaBH(OAc)$_3$, DCE
(iv) MsCl, py
(v) (PhO)$_2$PON$_3$, DBU, DMF, 60° C.
(vi) NaN$_3$, DMF, 60° C.
(vii) H$_2$, Pd black, EtOAc

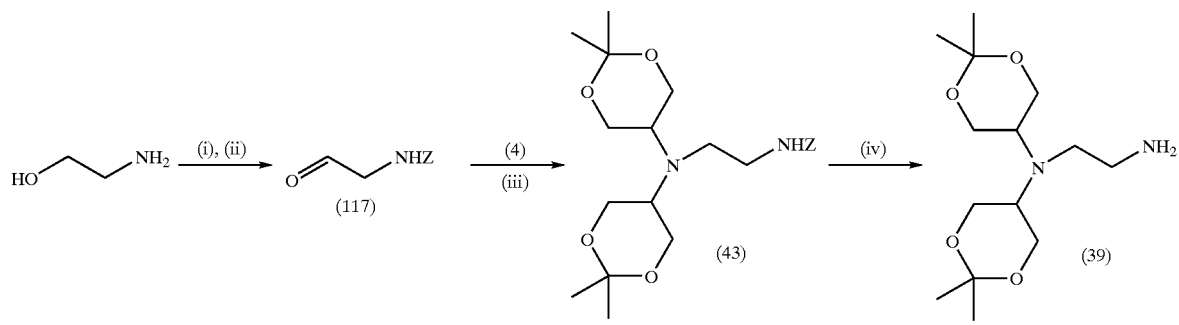

(i) PhCH$_2$OCOCl, Na$_2$CO$_3$, 1:1 dioxane/H$_2$O
(ii) PCC, DCM
(iii) NaBH(OAc)$_3$, DCE
(iv) H$_2$, Pd black, EtOAc Reductive amination of (4) with (44) or (45), both devived from lactone (46), provides alternative routes to alcohol (47). The OH group can be converted into a leaving group using known methodolgy and displaced with azide to give (48). Reduction of the azide group to the corresponding amine would provide a homologue to amine linkers (12) and (39).

Scheme 10
Further reductive aminations

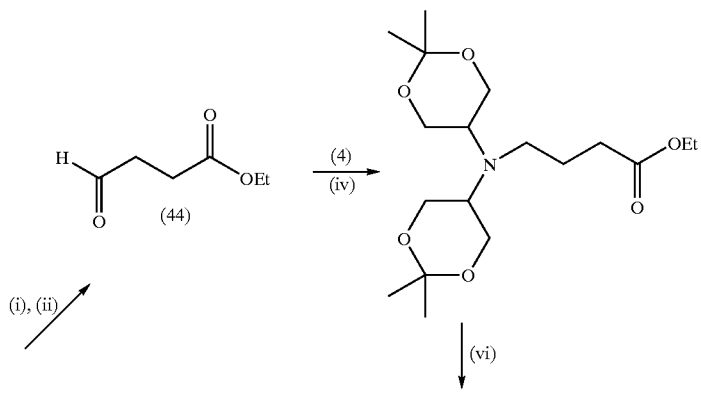

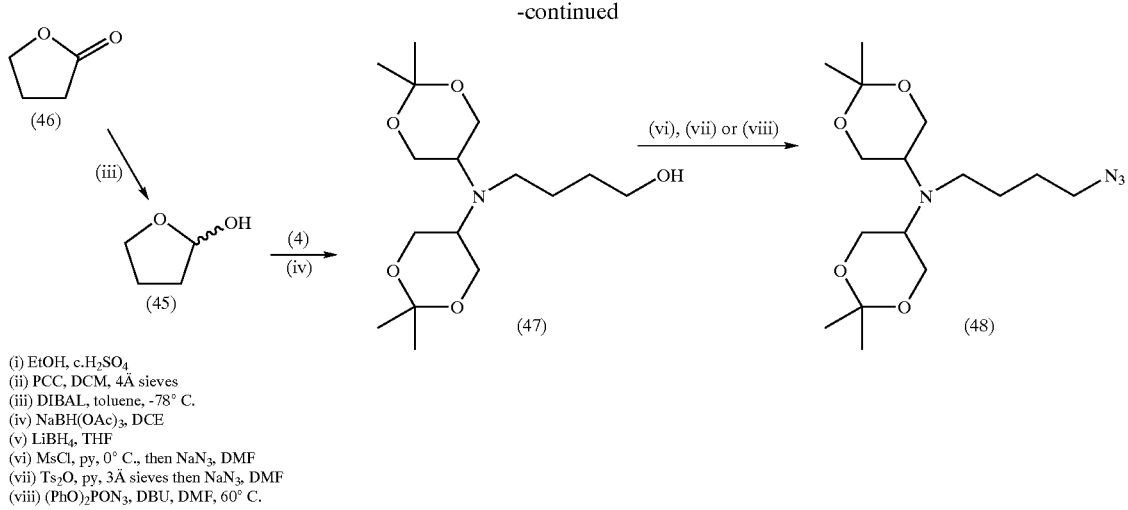

(i) EtOH, c.H₂SO₄
(ii) PCC, DCM, 4Å sieves
(iii) DIBAL, toluene, -78° C.
(iv) NaBH(OAc)₃, DCE
(v) LiBH₄, THF
(vi) MsCl, py, 0° C., then NaN₃, DMF
(vii) Ts₂O, py, 3Å sieves then NaN₃, DMF
(viii) (PhO)₂PON₃, DBU, DMF, 60° C.

Scheme 11 illustrates preparation of an alternative linker (49) to those illustrated in Scheme 5 via reductive amination using aldehyde (50).

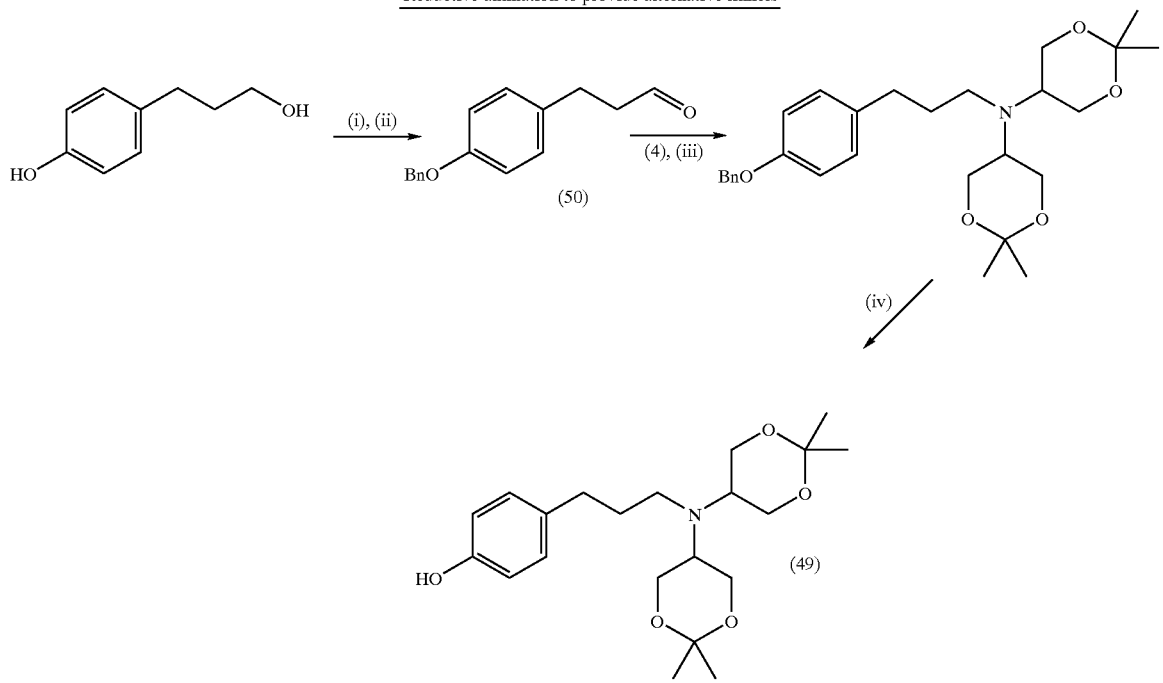

Scheme 11
Reductive amination to provide alternative linkers (i) BnBr, NaH, DMF
(ii) PDC, DCM
(iii) NaBH(OAc)₃, DCE
(iv) H₂, Pd black, MeOH Reductive amination [Scheme 12] of dihydroxyacetone or its equivalents with amines (51), rather than ammonia would also give rise to substituted materials such as (52) and (53) where R* can be straight chain, branched, cyclic, or aromatic amines, or any other amine, and X" is any suitable anion, for example halide or acetate. For example, reductive amination of dihydroxyacetone with butylamine would give N-bis(1,3-dihydroxyprop-2-yl)butylamine. Some other examples would be the reductive amination of long chain diamines such as (54) which would allow the formation of structures such as (55) with long lipophilic chains with basic and highly hydroxylic end groups. Such materials could also be sulfated and may have applications in the generation of micelles and/or of detergents.

Scheme 12
Reductive amination of diamines to highly divergent dendritic units

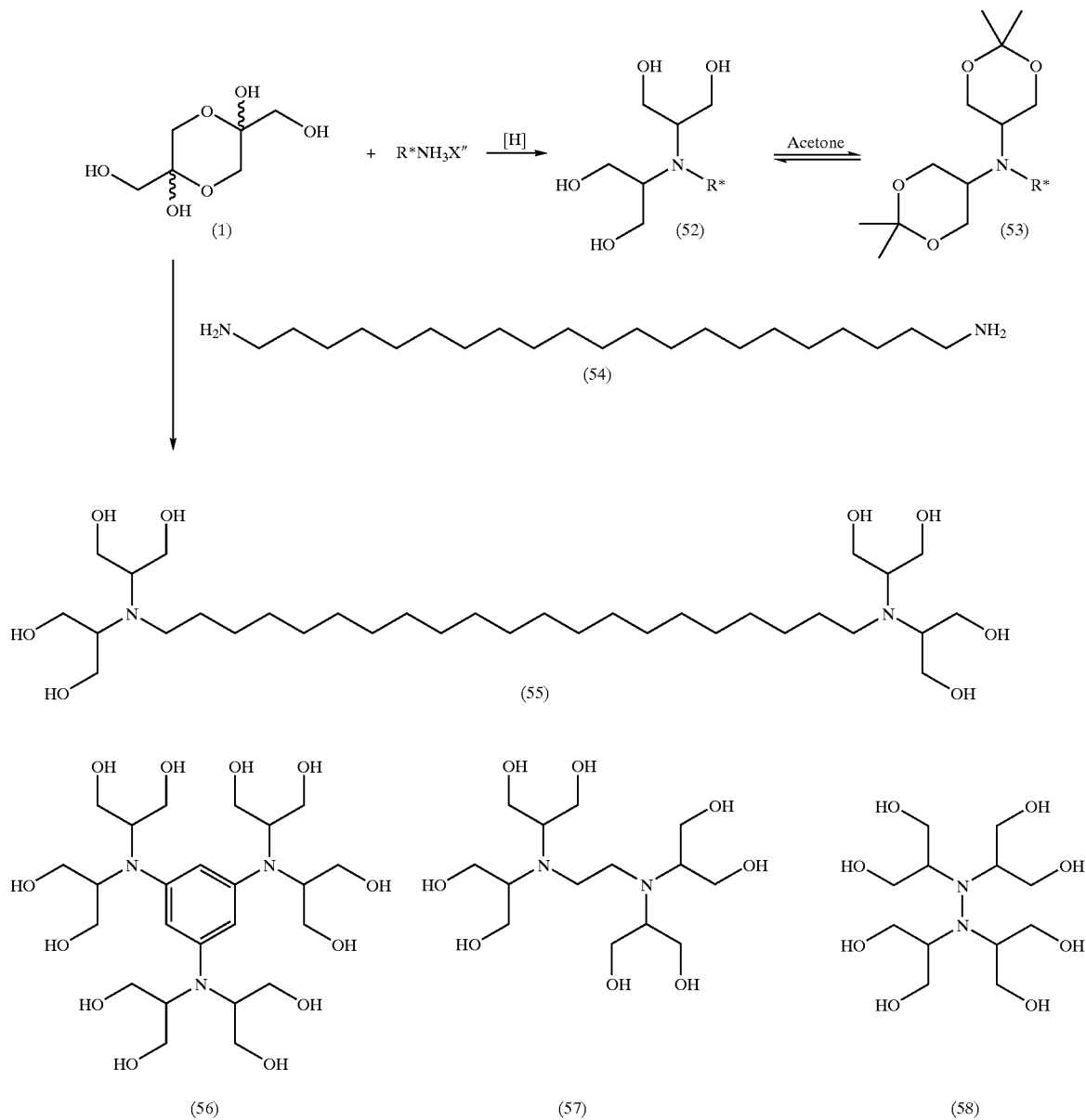

Alternatively highly branched structures might be derived from aromatic amines to give structures such as (56) from triaminobenzene, or (57) from ethylamine, or (58) from hydrazine. Many of these and related structures, including but not confined to (39), may provide powerful ligands for metals themselves, or allow the easy formation of relatively small branched structures with a very large number of phosphine, amine or sulphide groups providing a new and broad range of ligands for catalysts.

An alternative strategy would be to use the diacetonide (4) or a suitably protected equivalent thereof in the reductive amination of an aldehyde. Thus for example an alternative approach to compound (57) would be via the reductive animation of glyoxal (CHOCHO) with compound (4), followed by deprotection of the hydroxyl groups.

Further examples of readily available building blocks are illustrated in Scheme 13. Thus one of the dendritic units could be linked as an amine and the other as an amide (59) to allow choice of the basicity and ionisation state of the dendritic unit. Novel and chiral ligands possessing many coordinating hydroxyl groups together with amines (60) could be readily prepared. Acid halides of other oxyacids would also provide novel units. For example reaction of (4) with $PCl_3$ followed by deprotection would give the novel phosphoramidate (61). Sulphonamides such as (62) could be produced by reaction of (4) with a suitable sulphonyl chloride and would provide a further functional group for the base dendrimer units. Aromatic centres to the dendritic units would be readily available providing highly dendritic units in one step such as the tris-urea (63) from the triisocyanate, the tris amide (64) from mesitoyl chloride and the melamine derivative (65) available from cyanuric chloride.

Scheme 13
Further examples of possible dendritic units
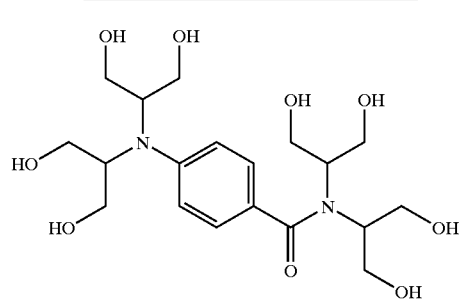
(59) mixing of dendrimer bonds
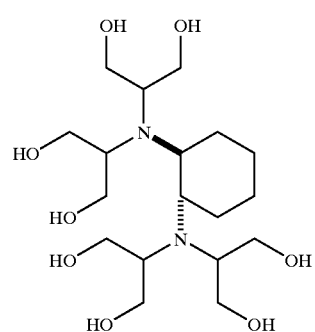
(60) opportunities for new catalysts
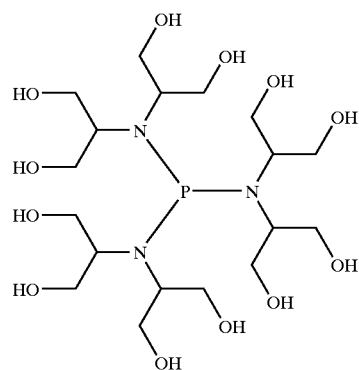
(61) new phosphoramidate
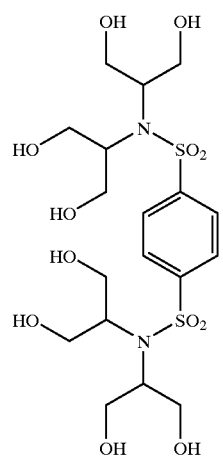
(62) sulfonamides
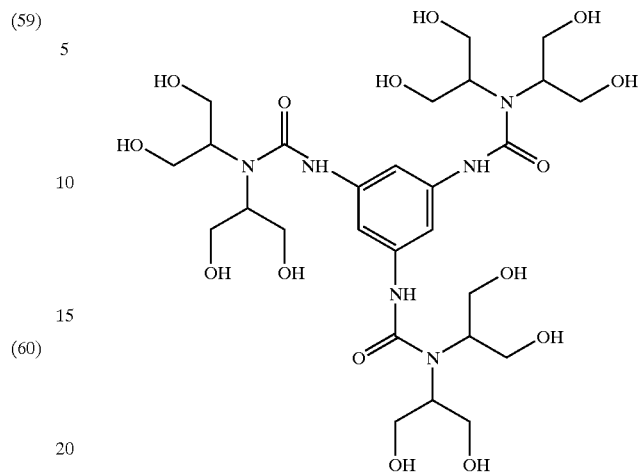
(63)
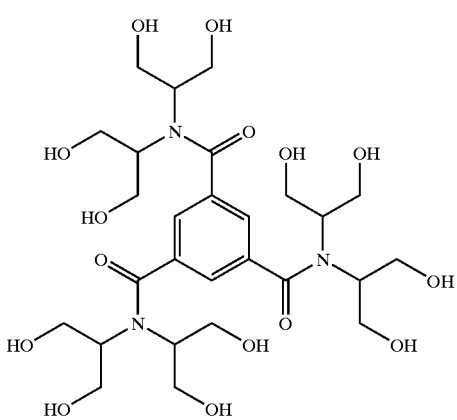
(64)
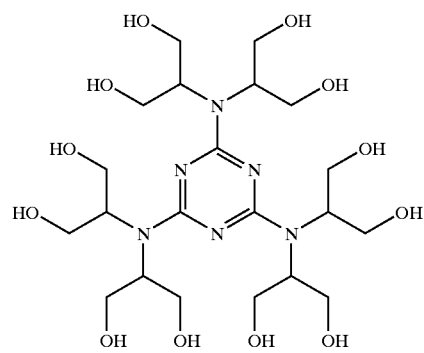
(65)

Scheme 14 illustrates the synthesis of various highly functionalised systems from cyanuric chloride. Diacetonide (4) or derivatives thereof such as (12), (39) or (49) may be reacted with cyanuric chloride (66) to give access to systems such as (67) and (68) which have potential uses as non-ionic surfactants (Scheme 14a) and to systems such as (69), (70) and (71) which on deprotection would give further dendritic units.

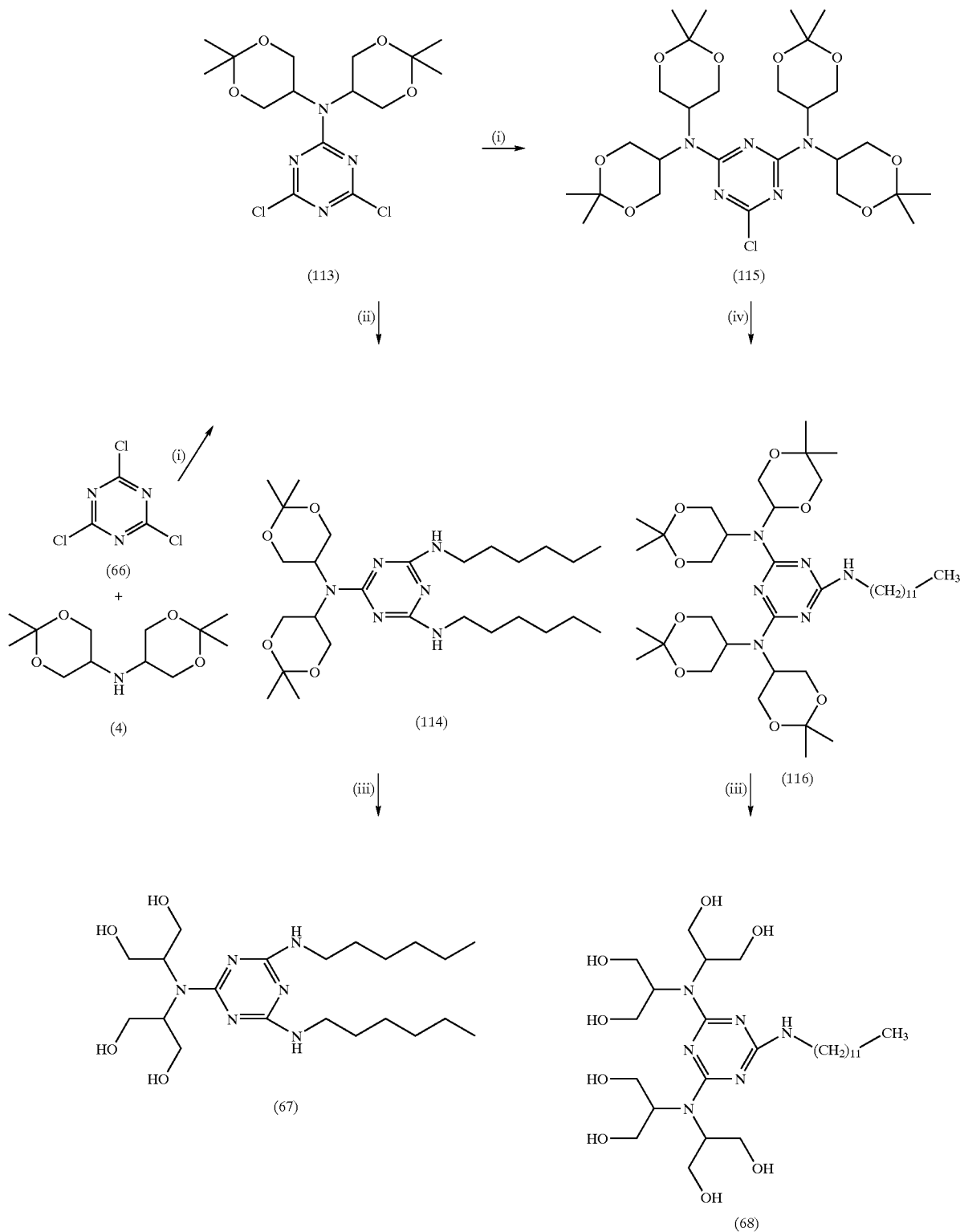

Scheme 14a (i) DIPEA, toluene, reflux (ii) CH$_3$(CH$_2$)$_5$NH$_2$, tolune, reflux (iii) AcOH, H2O (iv) CH$_3$(CH$_2$)$_{11}$NH$_2$, tolune, reflux Scheme 14
Reactions with cyanuric chloride
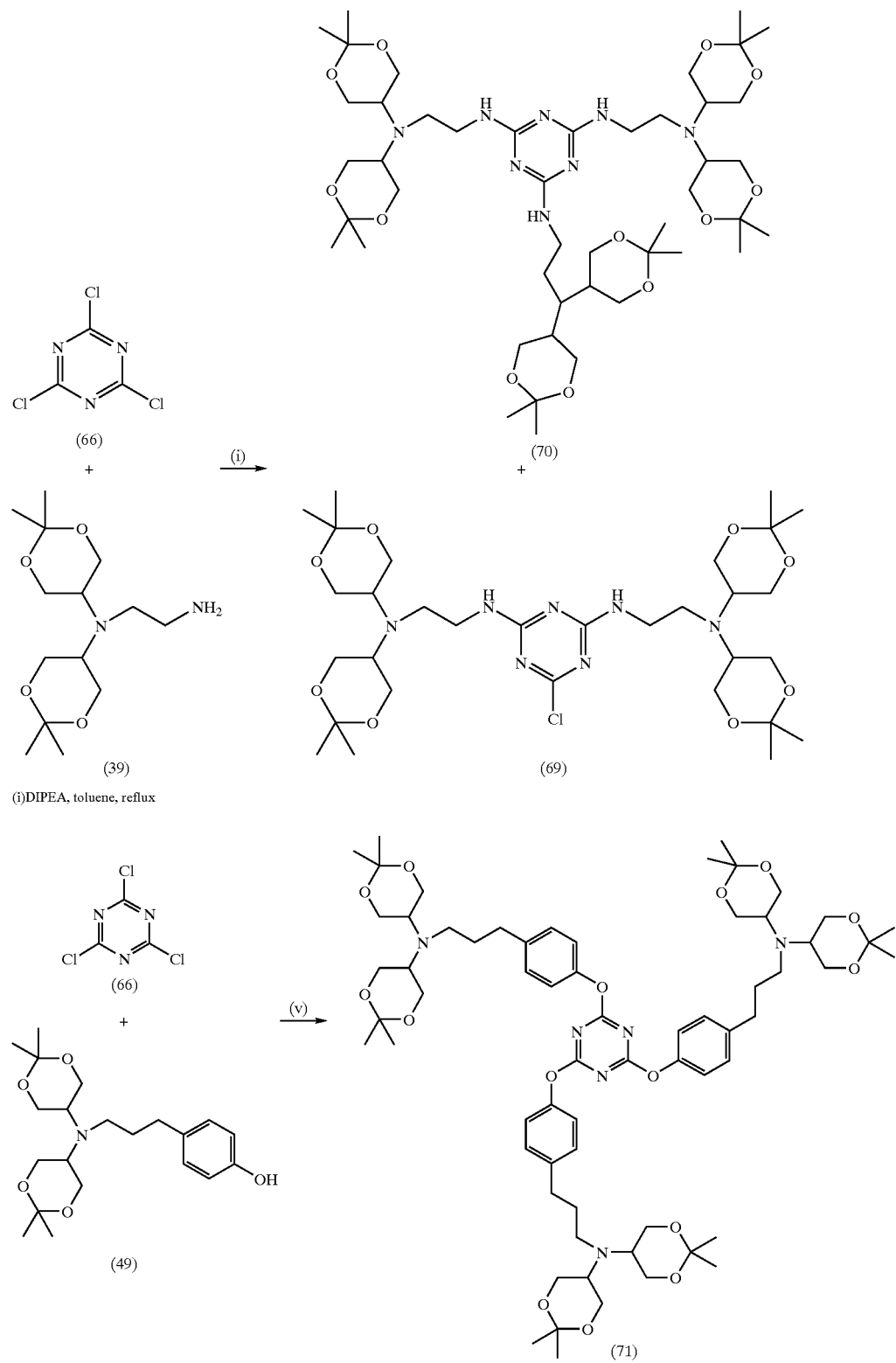
(i) DIPEA, toluene, reflux
(v) Me$_2$CO, K$_2$CO$_3$ Modified dendritic linkers such as amines (12) and (39) may also be elaborated or reacted in analogous ways to the diactonide (4). Thus, reaction of (39) with 1,4-benzene dicarbonyl or 1,3,5-benzene tricarbonyl gives access to dendritic core units such as (72) and (73) (Scheme 15). Use of (12) in place of, (39) gives the analogous systems with an extra methylene group in the alkylene chains linking the pairs of nitrogen atoms. Use of alcohol (10) in place of amine (39) gives a system with ester rather than amide linkages to the core aromatic ring.

Scheme 15
Reactions with benzene di- and tricarbonyl compounds

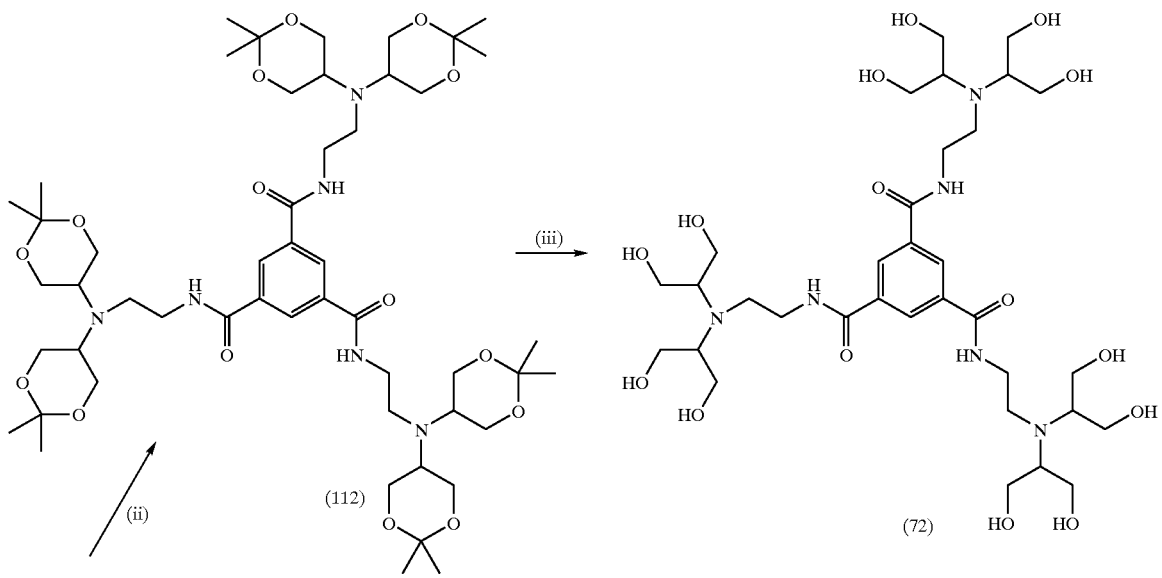

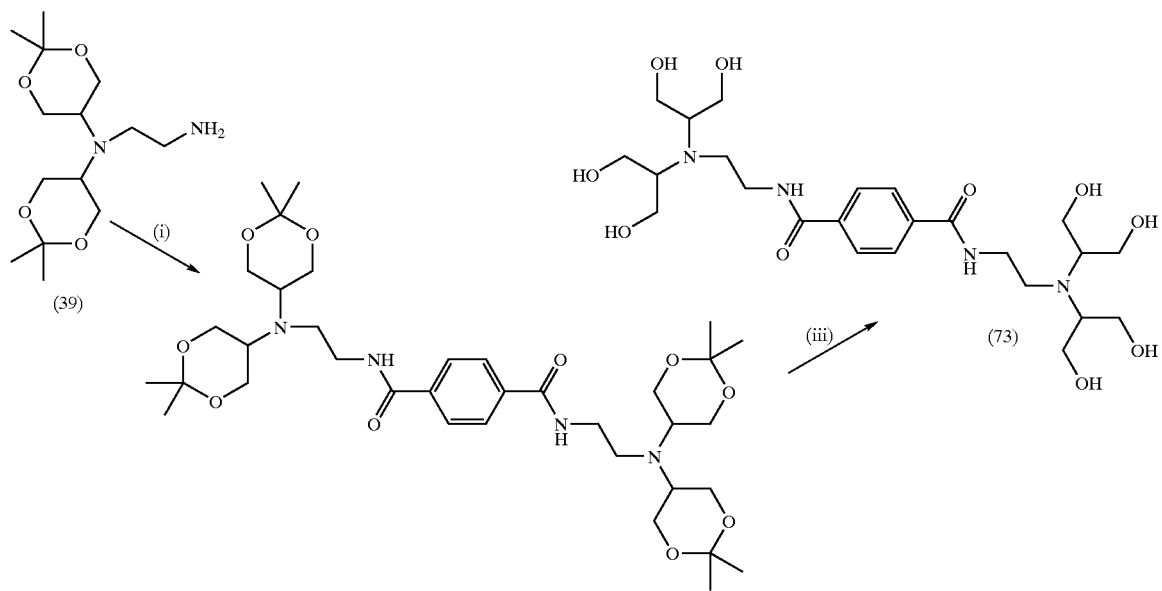

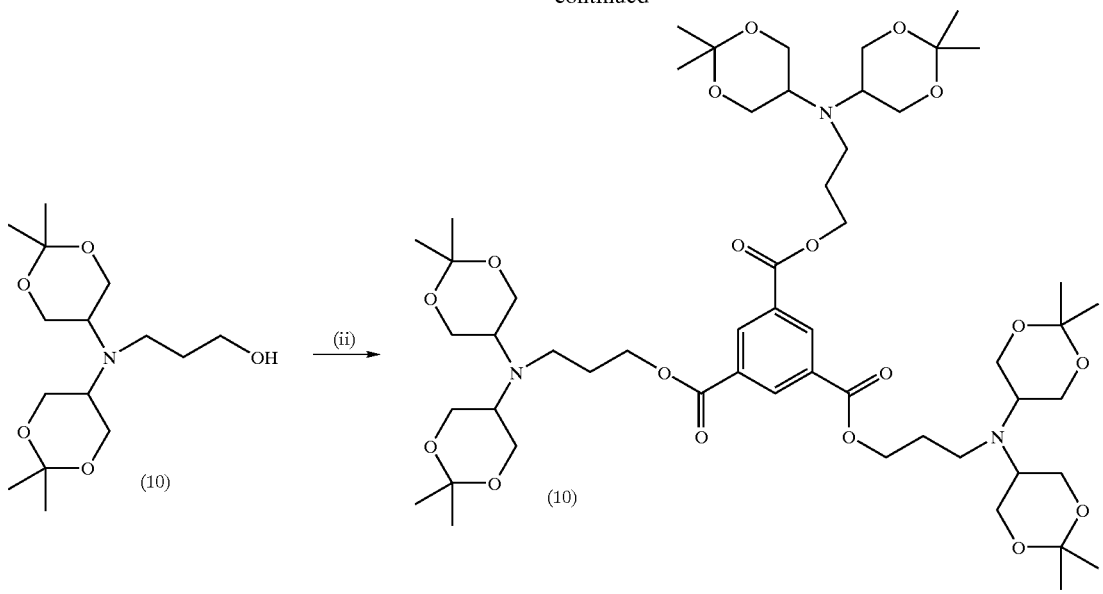

(i) 1,4-benzene dicarbonyl, DCM, EtN$_i$Pr, 0° C.
(ii) 1,3,5-benzene tricarbonyl, DCM, EtN$_i$Pr, 0° C.
(iii) TFA:H$_2$O Different derivatives of acetonide (4) may also be reacted together to form dendrimer units. For example as shown in Scheme 16, reaction of amine (12) with tosylate (74) gives the dendritic unit (75) which on deprotection would yield (76) with 12 free primary hydroxyl groups. Iteration of this procedure via conversion of the hydroxyl groups in (76) to tosylate groups and reaction with further amine (12) would give a highly branched structure with 48 primary hydroxyl groups on the outside of the dendrimer.

Scheme 16
Combination of different dendritic units

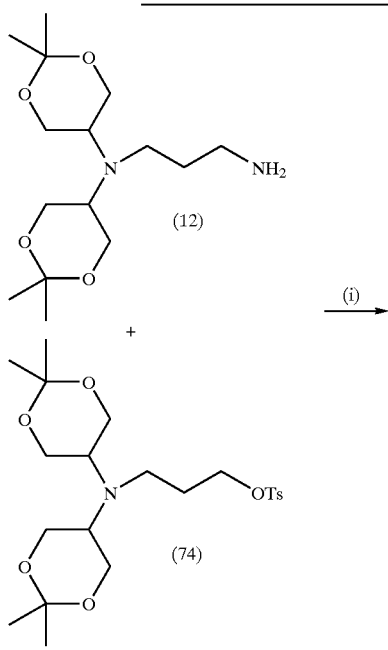

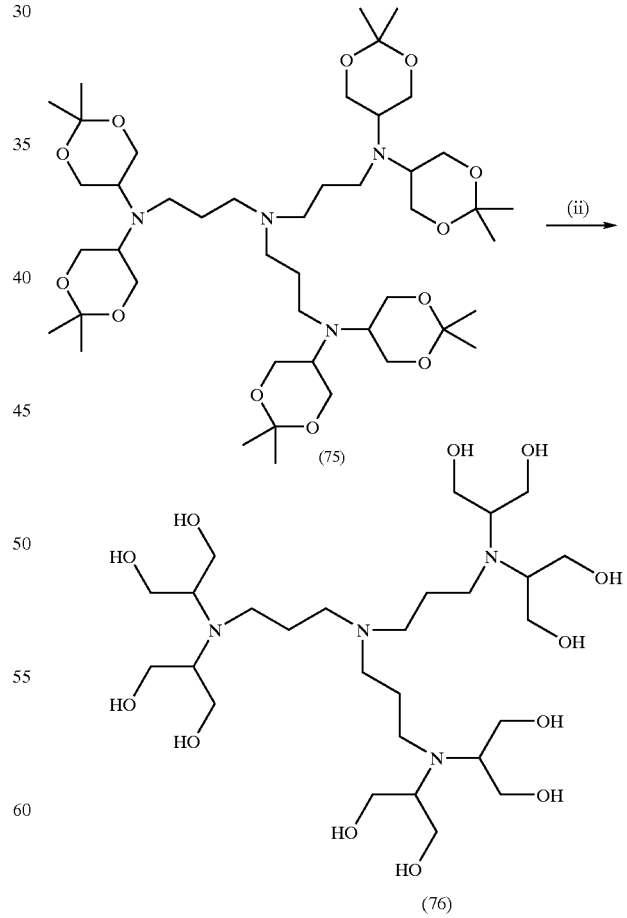

(i) DCM, EtN$^i$Pr2
(ii) TFA:H$_2$O

In addition to dendrimer core units, dendritic wedges may also be prepared from (3) or derivatives thereof, for example by elaboration of the hydroxyl groups as shown in Scheme 17. Conjugate addition of (3) to a suitable α,β-unsaturated ester leads to a tetraester (77). Hydrolysis of the ester groups followed by condensation of the liberated acid groups with amine (39) leads to a dendritic wedge structure (79).

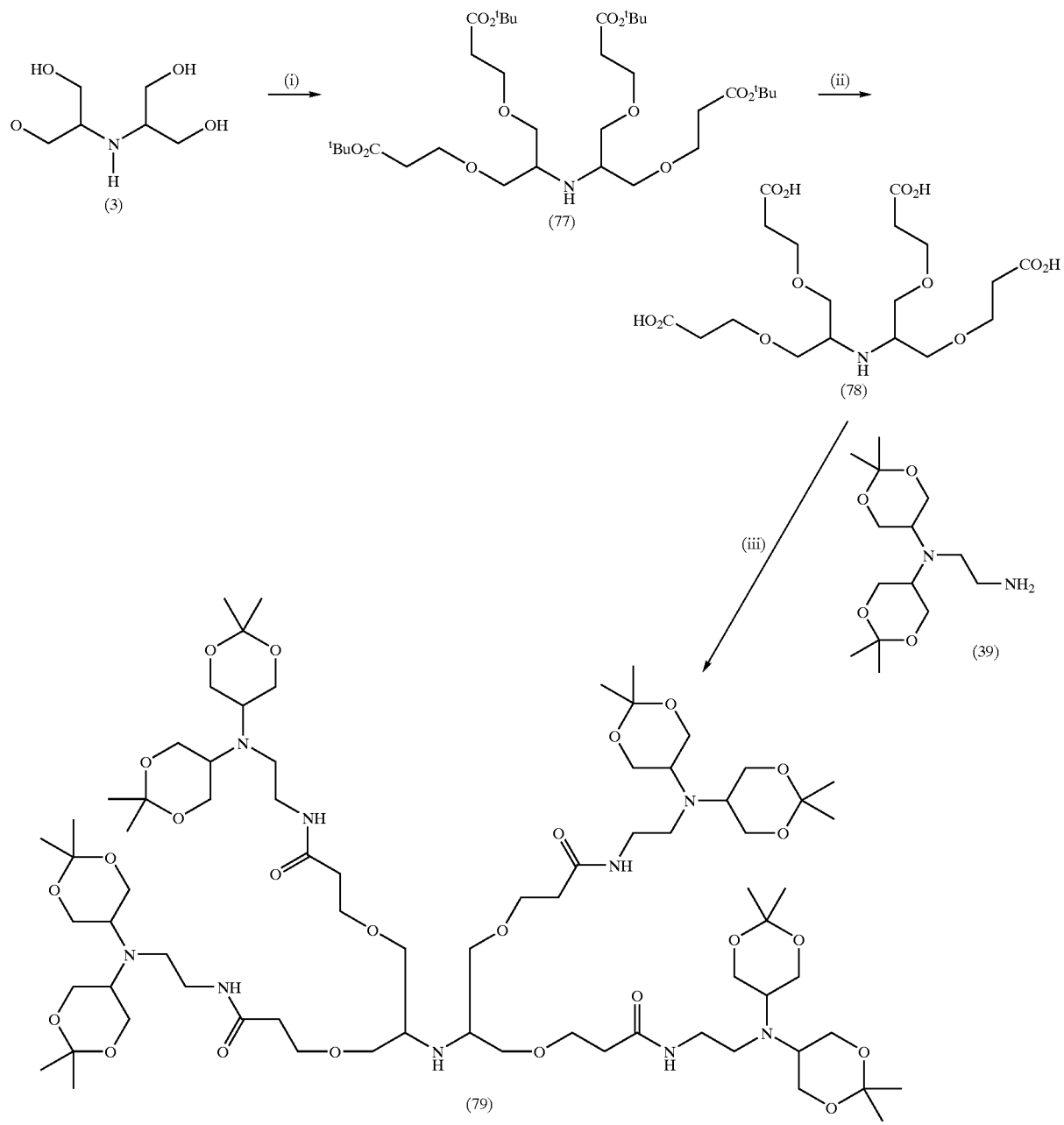

(i) $CH_2\!=\!CHCO_2{}^tBu$, 50% NaOH, $^nBu_4NHSO_4$
(ii) TFA:DCM, 1:1
(iii) TBTU, DMF, $EtN^iPr_2$ Other dendritic wedges may be prepared by reacting together dendritic units such as (80) and (81) as shown in Scheme 18.

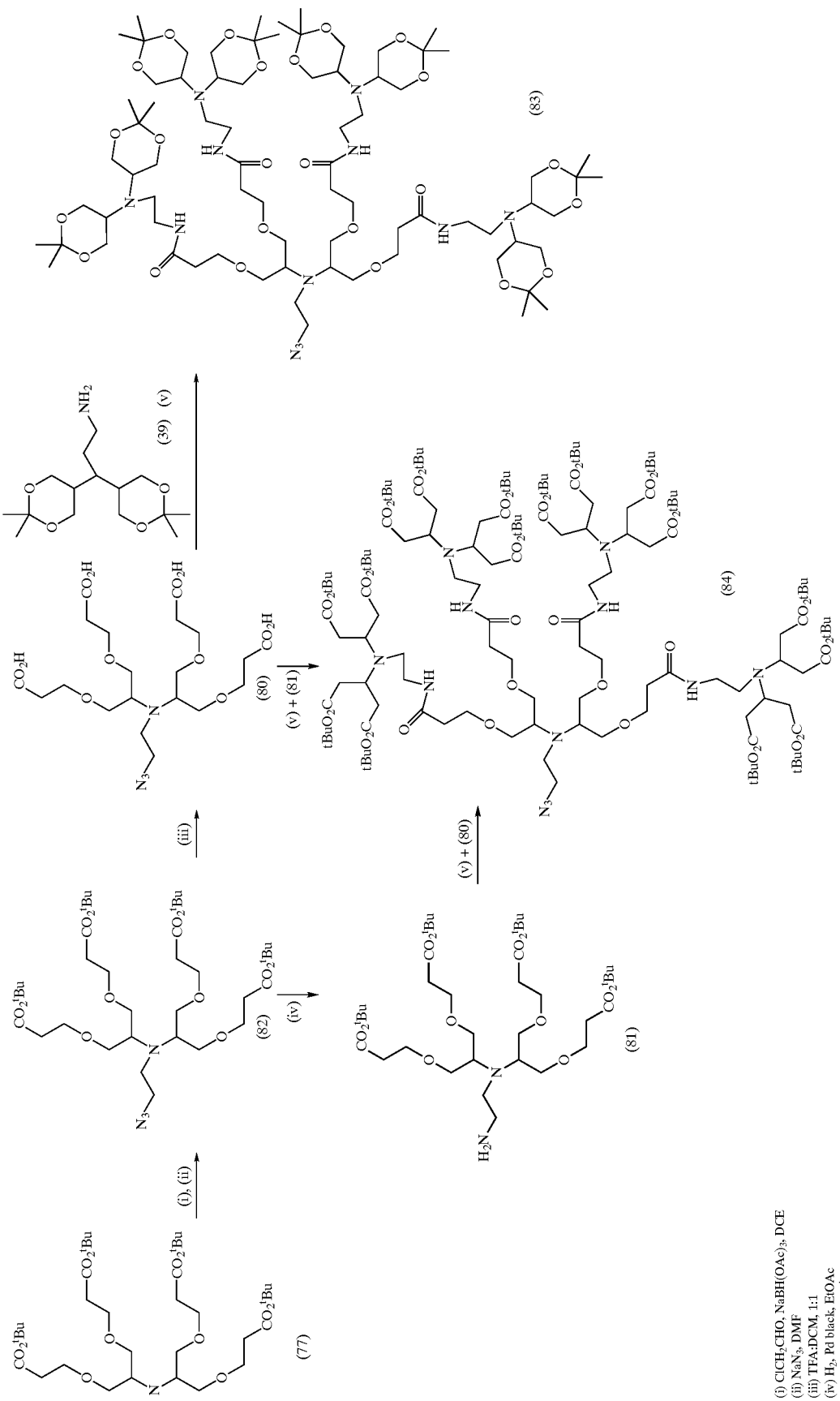

Dendritic units such as (81) can also be condensed with aromatic acid chlorides such as (85) to yield after deprotection a highly functionalised first generation dendrimer (86).
Reaction with (39) then leads to the protected even more highly functionalised second generation dendrimer (87) (Schemne 19).
Scheme 19
First and second generation dendrimers
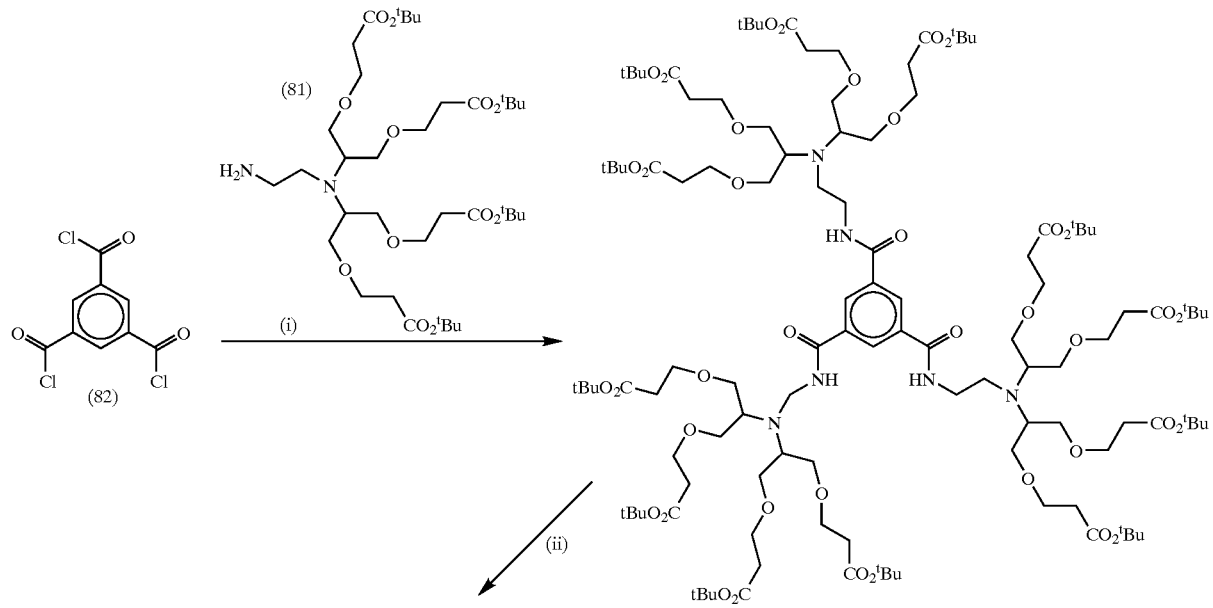
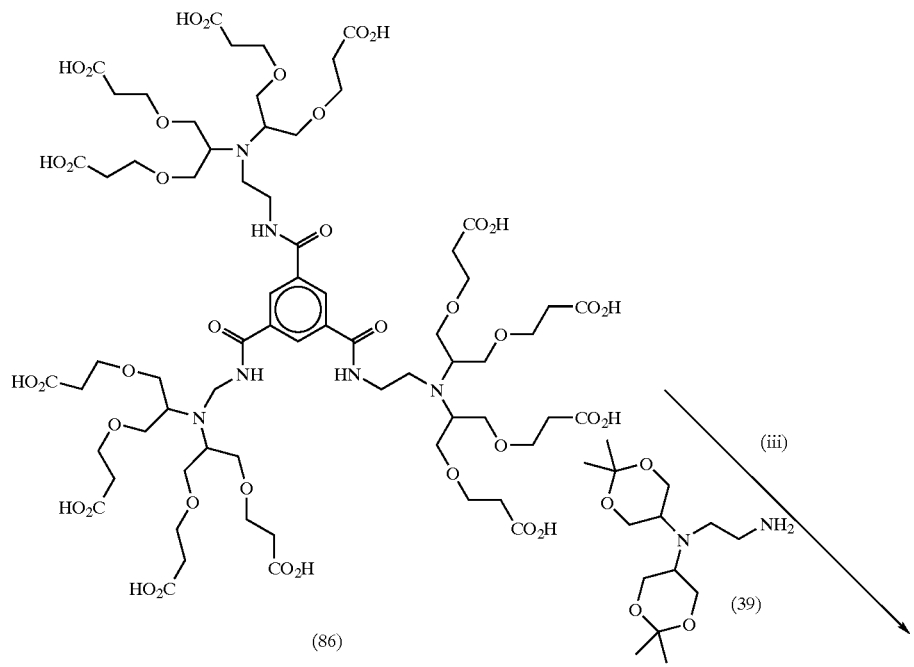

-continued
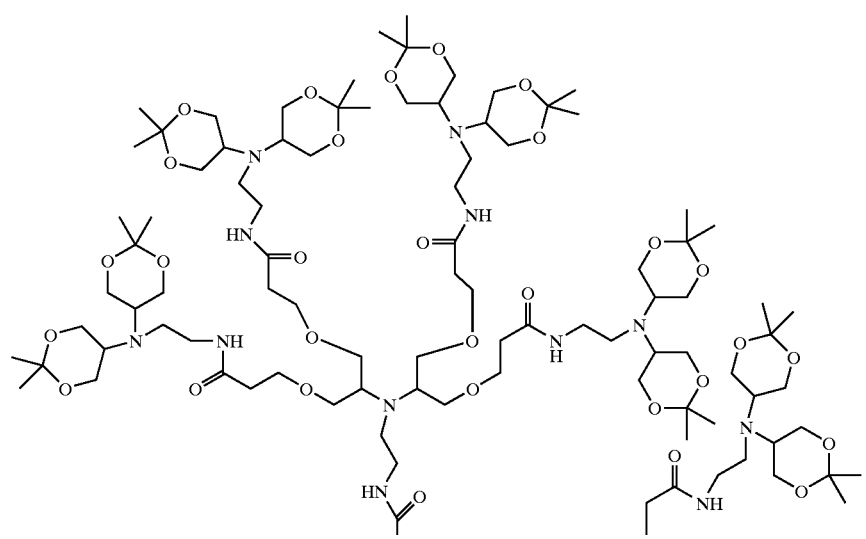
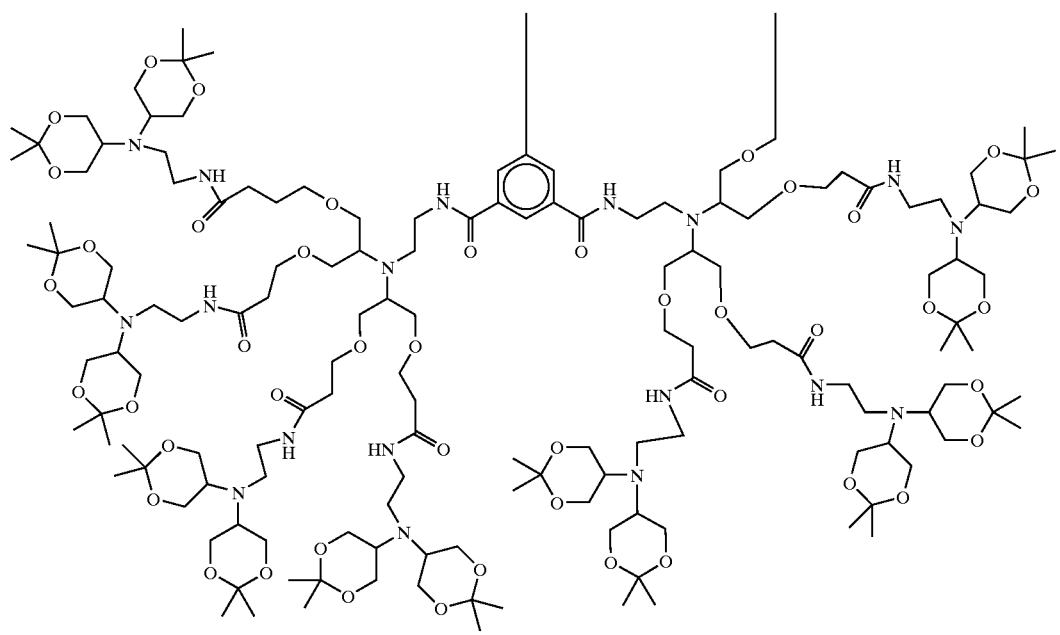
(87)
(i) DCM, EtNPr<sup>i</sup><sub>2</sub>, 0° C.
(ii) TFA:DCM, 1:1
(iii) TBTU, DMF, EtN<sup>i</sup>Pr<sub>2</sub>

An example of further elaboration of the free hydroxyl groups is shown in Scheme 20 in which reactive electrophiles such as the isocyanate (88) could react with (33) to form highly branched systems such as (89) bearing functional groups on the outside of the structure.

Scheme 20
Example of formation of urethane dendrimers from trimer (33)

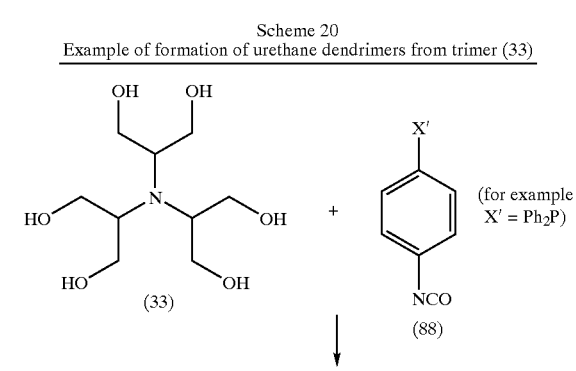

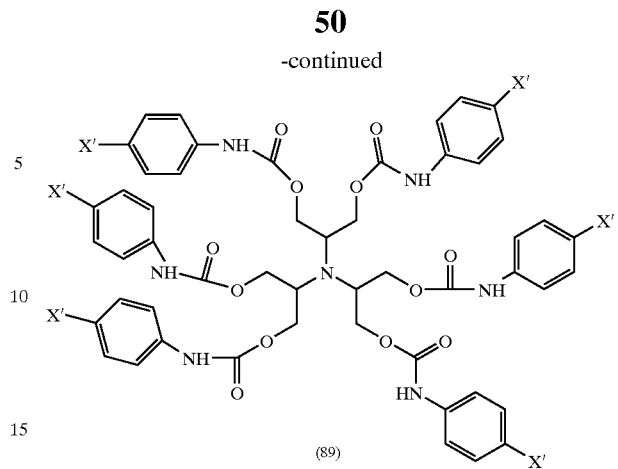

Easy access to the most highly branched and functionalised symmetrical dendrimers is illustrated in Scheme 21 by the combination of the trimer (33) with the acid chloride (17) to give (90), deprotection of which would give (91) with 24 primary hydroxyl groups; iteration of this procedure once would give a highly branched structure with 96 primary hydroxyl groups at the edge of the dendrimer. Many variations using longer spacer arms and different connecting groups, and allowing linking groups within the substructures will make this a very versatile synthesis of very highly branched and symmetrical dendrimers. The advantage is that fairly high molecular monomers with very many functional groups and well defined chemical structures would be readily available.

Scheme 21
Very highly branched symmetrical dendrimers

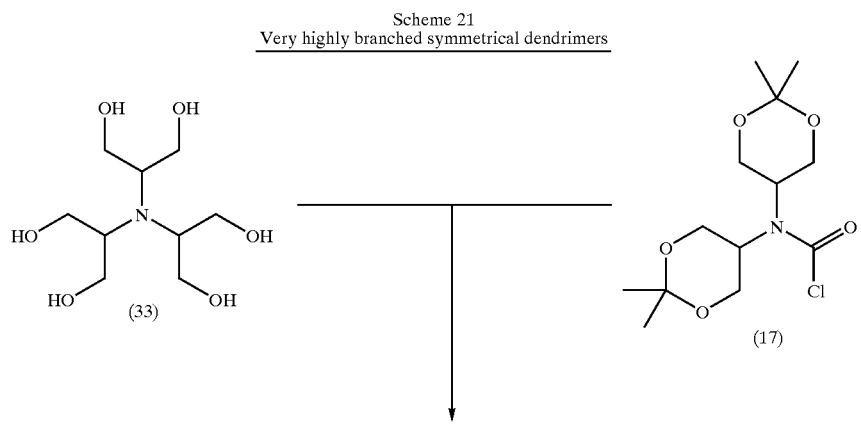

-continued
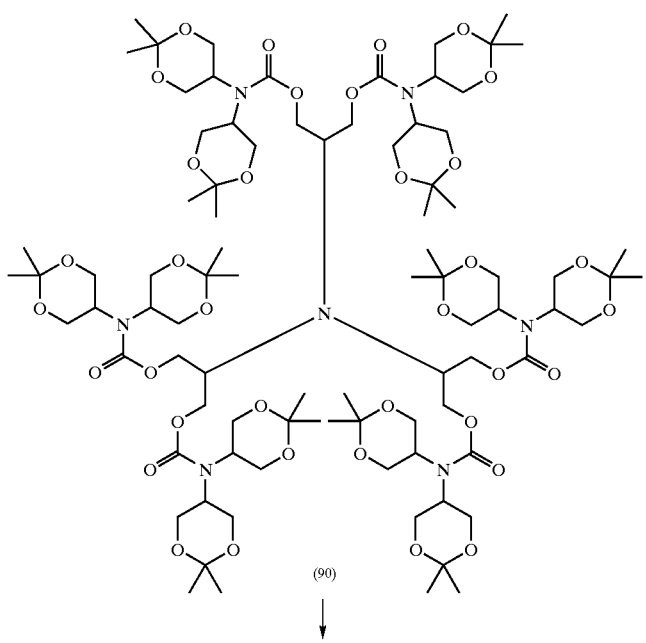
(90)
↓
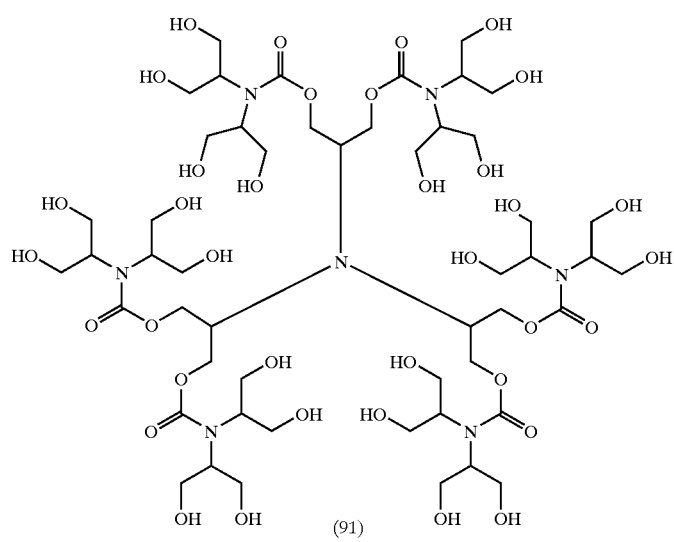
(91)
with 24 primary alcohols
(repeat to produce higher generation dendrimers
with large numbers of primary alcohols on the outer surface)

The carbonate dendrimer (92) could give easy access to unsymmetrical dendrimers as indicated in Scheme 22. Thus treatment of (92) with an amine would give the urethanes (93) with just half of the dendritic hydroxy groups functionalised and the other remaining free, either to be differentially functionalised or left as primary alcohols.

Thus Scheme 23 indicates a number of structures readily available from (4) or a suitably protected equivalent thereof, including a simple glucose derivative (94), available for example by conversion of the primary hydroxyl group of glucose to a leaving group followed by displacement by (4). Similarly, an amide unit at C-6 of glucose could be intro-

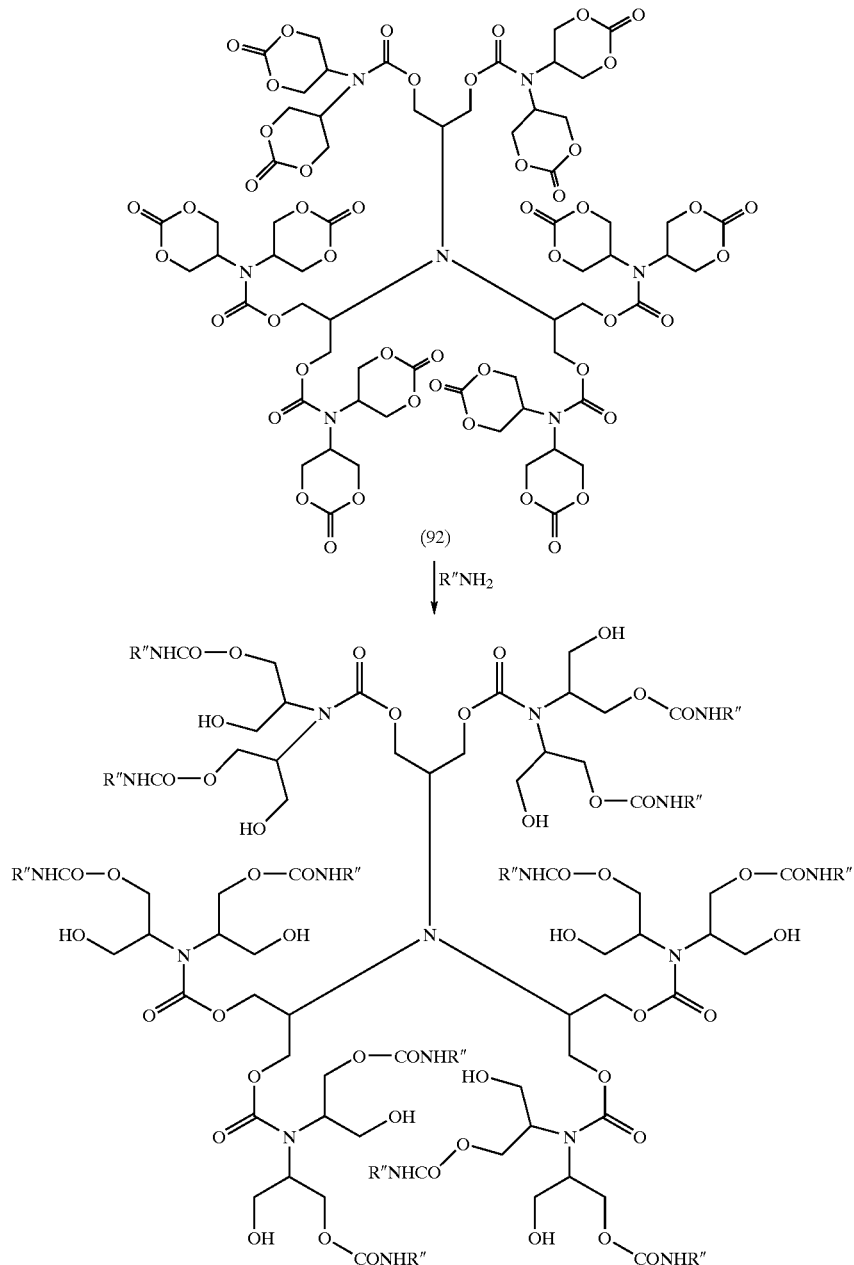

Scheme 22
Very highly branched unsymmetrical dendrimers

Another major area of likely potential application of the diacetonide (4) and related linkers is in the generation of novel sugar structures. Three classes of such materials may be prepared (i) derivatives of monosaccharides and of oligosaccharides incorporating in particular the diacetonide motif, including (ii) derivatives of cyclic aminosugars and (iii) novel dendritic structures.

duced as in (95) via reaction of (4) with glucuronolactone. Reduction of (95) would give an alternative route to compound (94). N-acetylglucosamine or a suitably protected derivative thereof could be used as the amine component in the monoreductive amination of dihydroxyacetone, followed by N-acylation to give (96). As anyone skilled in the art of carbohydrate chemistry will appreciate there are many alternative modifications to monosaccharides and related materials, to many sugars including but not confined to glucose, galactose, fucose, rhamnose, mannose, ribose in both their pyranose and furanose forms and of related C-glycosides and other derivatives thereof.

Further modified monosaccharides are illustrated by derivatives such as (97) as a ribose analogues and mono amine derivatives such as fructose analogue (98) and the symmetrical structure (99) which could be considered as a dendrimer of a C-glycoside of D-ribose. Compounds such as (97), (98) or (99) would be available for example by reaction of (4) (or a suitably protected equivalent thereof) with an acyl chloride group at the relevant position of a (suitably protected) monosaccharide, followed by reduction of the amide to the corresponding amine. Alternatively, compounds such as (4) could be used in the reductive amination of an aldehyde functionality at the relevant position of a (suitably protected) monosaccharide. Suitable protecting groups for use in carbohydrate chemistry are well known in the art.

Scheme 23
Modified monosaccharides including novel dendrimers

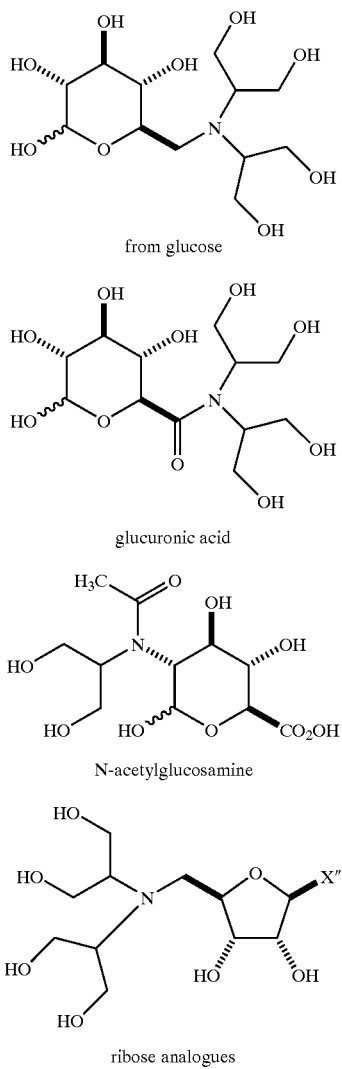

(94) from glucose

(95) glucuronic acid

(96) N-acetylglucosamine

(97) ribose analogues

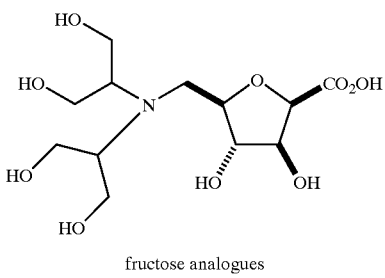

(98) fructose analogues

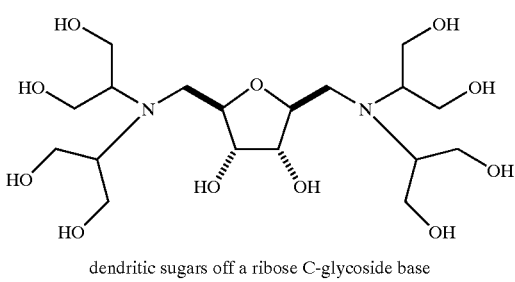

(99) dendritic sugars off a ribose C-glycoside base

As mentioned above iminosugars are a general family of glycosidase inhibitors, and additionally inhibit other sugar metabolising enzymes with applications as diverse as the inhibition of glycosyl transferases, the inhibition of the biosynthesis of the cell walls of various organisms including mycobacteria as an approach to the treatment of tuberculosis, leprosy and related diseases, and of very many other process involving sugars. Modification of such materials by the introduction of the optionally protected N-1,3-dihydroxyprop-2-yl group would provide a new range of sugar analogues [Scheme 24]. Such groups would, for example, be introduced into a (suitably protected) imino sugar by using the imino sugar as the amine component in the reductive amination of 1,3-dihydroxyacetone. In such reactions, imino sugars with a second amine functionality could have one nitrogen atom selectively protected thus allowing selective derivatisation of the other nitrogen atom. This would allow access to compounds such as (107) or (108) below, where the side chain amine functionality is derivatised but the ring nitrogen is not.

Scheme 24
Modified amino sugars

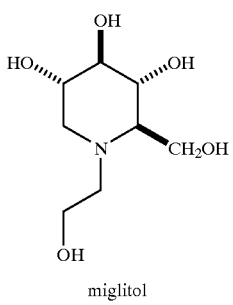

(101) miglitol

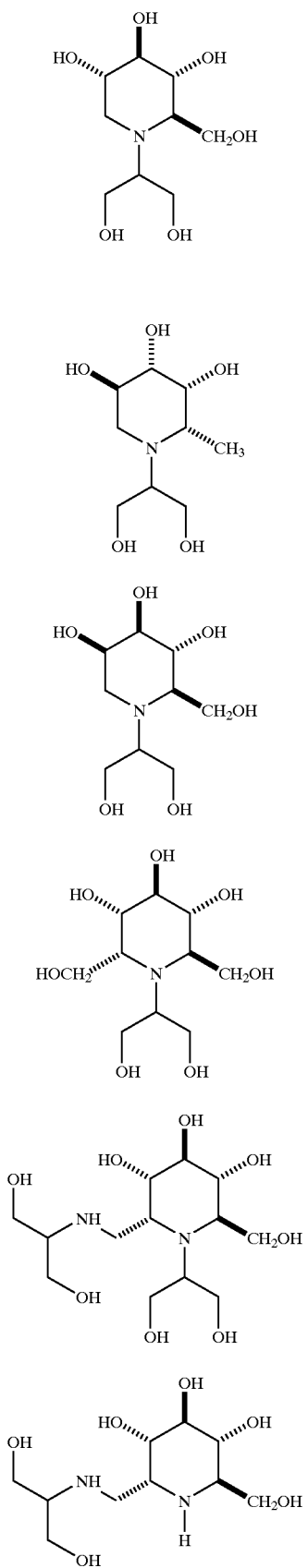

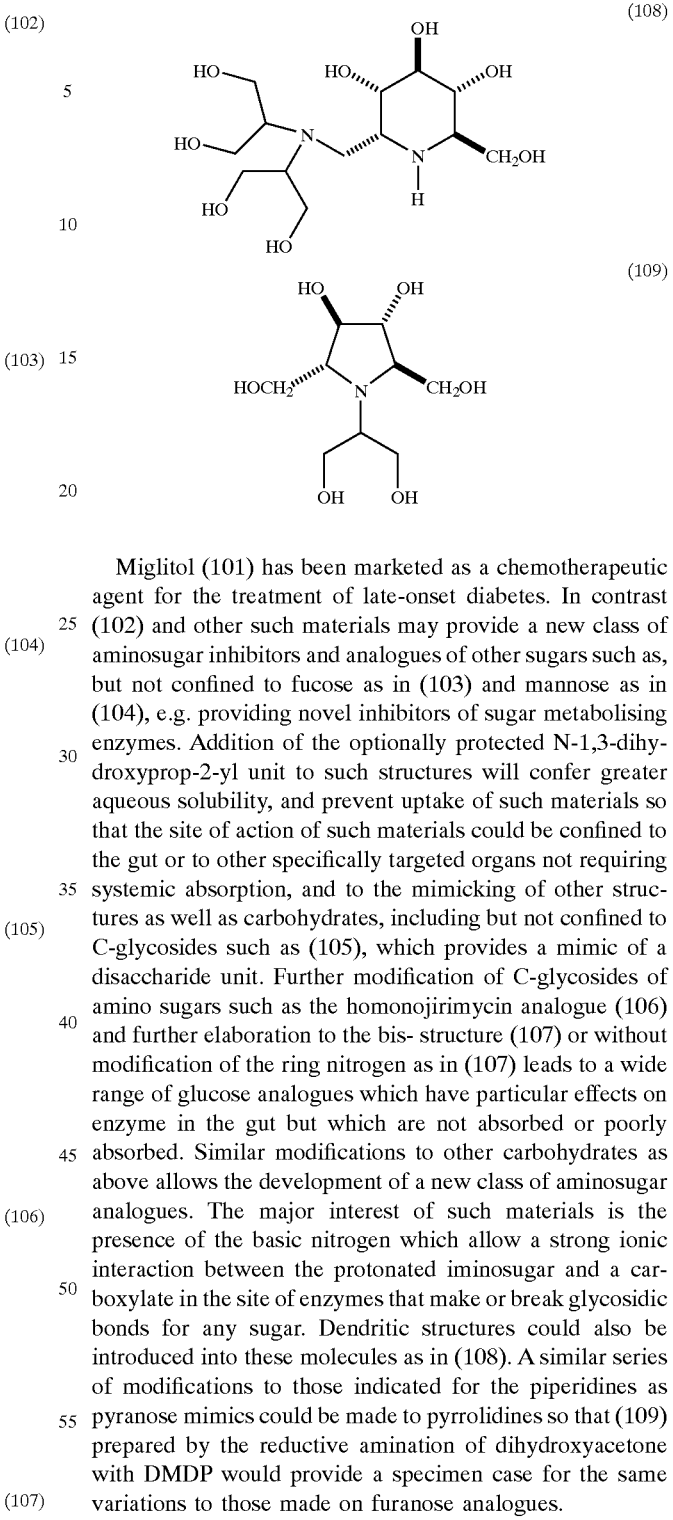

Miglitol (101) has been marketed as a chemotherapeutic agent for the treatment of late-onset diabetes. In contrast (102) and other such materials may provide a new class of aminosugar inhibitors and analogues of other sugars such as, but not confined to fucose as in (103) and mannose as in (104), e.g. providing novel inhibitors of sugar metabolising enzymes. Addition of the optionally protected N-1,3-dihydroxyprop-2-yl unit to such structures will confer greater aqueous solubility, and prevent uptake of such materials so that the site of action of such materials could be confined to the gut or to other specifically targeted organs not requiring systemic absorption, and to the mimicking of other structures as well as carbohydrates, including but not confined to C-glycosides such as (105), which provides a mimic of a disaccharide unit. Further modification of C-glycosides of amino sugars such as the homonojirimycin analogue (106) and further elaboration to the bis- structure (107) or without modification of the ring nitrogen as in (107) leads to a wide range of glucose analogues which have particular effects on enzyme in the gut but which are not absorbed or poorly absorbed. Similar modifications to other carbohydrates as above allows the development of a new class of aminosugar analogues. The major interest of such materials is the presence of the basic nitrogen which allow a strong ionic interaction between the protonated iminosugar and a carboxylate in the site of enzymes that make or break glycosidic bonds for any sugar. Dendritic structures could also be introduced into these molecules as in (108). A similar series of modifications to those indicated for the piperidines as pyranose mimics could be made to pyrrolidines so that (109) prepared by the reductive amination of dihydroxyacetone with DMDP would provide a specimen case for the same variations to those made on furanose analogues.

A third class of carbohydrate structure would be sugar dendrimers based on the reductive amination products of dihydroxyacetone. For example, amines produced by the monoreductive amination would have two free hydroxyl groups which could be joined to the anomeric or other positions of carbohydrates and carbohydrate mimetics, giving a very wide range of materials. Again the illustrations in Scheme 23 are all given for the anomeric position of glucose; it is clear that other sugars could be used for such structure including mono-, di- and oligo-saccharides, other sugar mimics including azasugars and C-glycosides, and that attachments can be made at other than the anomeric position. Structure (110) shows a disaccharide equivalent which can have varied R''' substituents and could for example be linked to beads, to columns, or to proteins for a wide variety of applications including the possibility of providing antibodies to carbohydrates. The surfaces of the solid support or of the protein would have a very high density of a specific carbohydrate recognition site.

Structure (115) shows a dendritic structure in which the tetraglycosylated equivalent of p-phenylene diamine has a dendritic framework, and a highly dendritic carbohydrate structure such as (111) could be provided by a spacer derivative of (4) with a trisubstituted aromatic compound.

Scheme 25
Dendritic sugars (110)

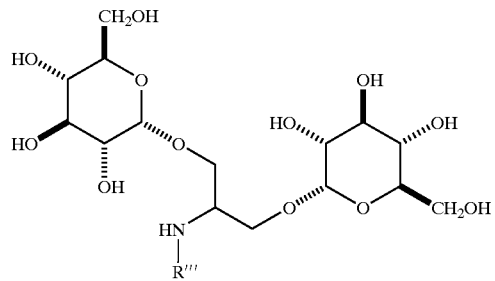

(115)

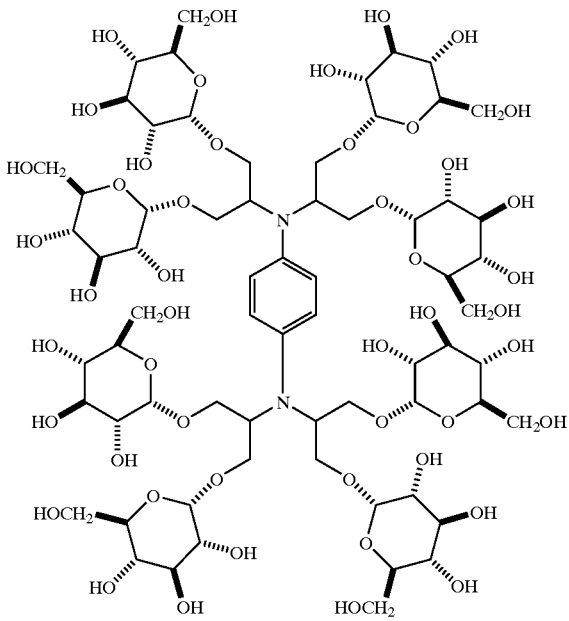

(111)

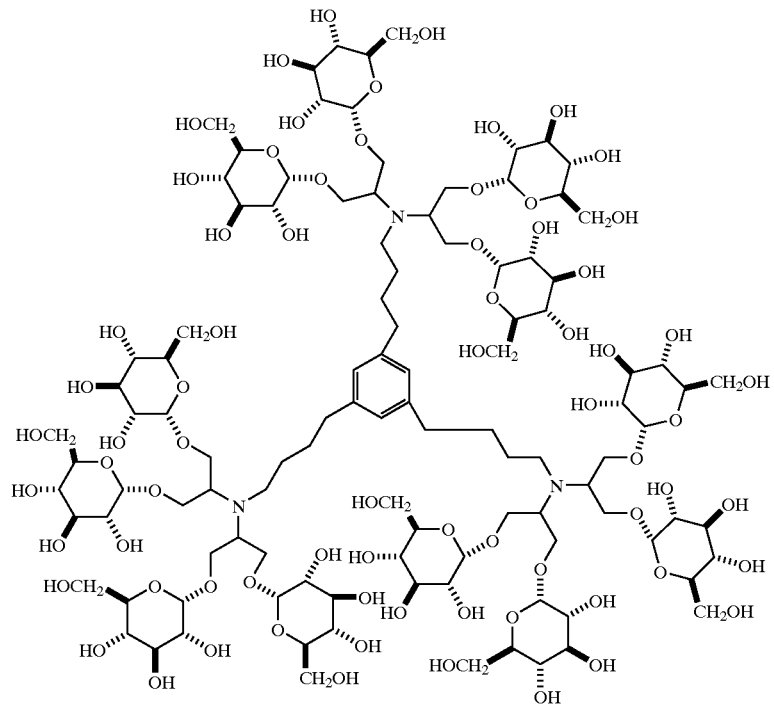

Such materials may be added onto beads in order to increase the availability of the functional groups at the surface of the bead, depending on how the structure is modified by the attachment of the dendrimer to the surface. Other ligand properties of dendrimers are currently the subject of many investigations (such as Zimmerman et al., Tetrahedron Lett. 38: 5459 (1997)). There are many other properties of such branched structures. Thus other possible uses of the materials include (i) the generation of amphiphilic chains for use in micelle formation, (ii) as new surfactants, detergents or soaps which could be neutral or basic and positively or negatively charged, (iii) as solubilized analogues of less soluble materials, e.g by the inclusion of a highly hydroxylic group at the end of a peptide chain, and (iv) as new sugar dendrimers e.g. for generation of specific antibodies to sugar units, etc.

The invention will now be described further with reference to the following non-limiting Examples:

EXAMPLE 1 bis(1,3-dihydroxy-prop-2-yl)amine (3)

Method 1: Sodium cyanoborohydride (10.0 g, 159 mmol, 3 equivalents) was added to a solution of dihydroxyacetone dimer (28.67 g, 159 mmol, 3 equivalents) and ammonium chloride (2.84 g, 53 mmol, 1 equivalent) in methanol (400 ml) and acetic acid (40 ml). After stirring for 20 hours, aqueous hydrochloric acid (2M, 100 ml) was added and after stirring for 4 hours the reaction was concentrated in vacuo, dissolved in methanol (100 ml), filtered and concentrated once more. The viscous residue was dissolved in water and applied to an ion exchange column (Amberlite, IR120, H+), which was eluted first with water, and then with a solution of aqueous ammonia (1M0. The solvent was removed to give (3), a hygroscopic oil (7.49 g, 85%).

Method 2: The diacetonide (4) (107 mg, 0.436 mmol) was dissolved in aqueous acetic acid (10 ml, 80%) and stirred for 4.5 hours at 60–70° C. After concentration, the residue was purified by ion exchange chromatography (Amberlite IR-120, H+ form, eluted with 1 N ammonia solution). The alkaline solution was concentrated in vacuo to give bis-(1, 3-dihydroxy-isopropyl)-amine (3) (70 mg, 97%) as a colourless oil; m/z (APCI+) 165.8 (M+H+, 15%), 147.9 (M+H+–$H_2O$), 129.9 (M+H+–2$H_2O$); 103.7(100%); $^1$H NMR (200 MHz, $D_2O$): δ 2.85 (2H, app quint, J=5.3 Hz, NCH), 3.53 (4H, dd, J=5.5, $J_{gem}$=11.5 Hz, 4OCH), 3.61 (4H, dd, J=5.6 Hz, 4OCH); $^{13}$C NMR (50 MHz, $D_2O$): δ 58.1 (d, 2NCH), 61.8 (t, 4O$CH_2$).

EXAMPLE 2

Diacetonide (4) preparation

Method 1: Dihydroxyacetone dimer (5.60 g, 31.1 mmol) and sodium cyanoborohydride (2.4 g, 38.2 mmol) were added to a solution of ammonium fluoride (380 mg, 10.3 mmol) in methanol (100 ml). After 1.5 hours and the addition of acetic acid (10 ml) the clear solution was stirred for 24 hours. More sodium cyanoborohydride (1.20 g, 19.1 mmol) was added and the solution was stirred for a further 1.5 hour before the reaction was acidified with hydrochloric acid (30 ml, 2 N). After vigorous stirring with suction for at least 3 hours the solution was concentrated in vacuo. The solid residue was extracted with methanol (100 ml). After filtration and concentration the oily residue was redissolved in water (100 ml) and passed down a column (2.5×30 cm) with Amberlite (IR 120, H+-form). The elution with water was continued until the eluate coming of the column reacted neutral. The elution was continued with ammonia solution (1 N) and after a neutral prerun (~200 ml) the alkaline washings (~500 ml) were collected and concentrated to give 1.70 g of residue. The residue was dissolved in N,N-dimethylformamide (20 ml), acetone (80 ml) and 2,2-dimethoxypropane (20 ml). Sulfuric acid (2.5 ml, conc.) was added dropwise under vigorous stirring (an immediately formed precipitate dissolves again within 30 min) and the yellow solution was stirred at room temperature overnight. The acid was neutralised with an excess of sodium bicarbonate. After filtration and concentration in vacuo the remaining solid was suspended in hot acetone (ca. 100 ml). The insoluble salts were removed by a second filtration and the filtrate was concentrated. Purification by flash chromatography (toluene/acetone, 6:1) gave bis-(2,2-dimethyl-1,3-dioxane-5-yl)-amine (4) (922 mg, 37%) as a solid which can be recrystallised from hexane/ether: mp. 65° C. (plates, from hexane/ether); m/z (ES+) 284 (M+K+, 5%), 268 (M+Na+, 25%), 246 (M+H+, 100%); $^1$H NMR (500 MHz, acetone-d6): δ 1.30, 1.34 (12H, 2 s, 2C$Me_2$), 2.72 (2H, m, 2NCH), 3.51 (4H, dd, J=7.8, $J_{gem}$=11.6 Hz, 4OCH), 3.86 (4H, dd, J=4.8 Hz, 4OCH); $^{13}$C NMR (50 MHz, acetone-d6): δ 21.9, 26.1 (2 q, 2C$Me_2$), 49.5 (d, 2CHN), 65.1 (t, 4C$H_2$), 98.0 (s, 2C$Me_2$).

Method 2: Acetone (30 ml), 2,2-dimethoxypropane (10 ml) and concentrated sulphuric acid (1 ml) were added to a solution of (3) (1.71 g, 10.35 mmol) in DMF (10 ml) at room temperature. An initially formed precipitate gradually dissolved. The reaction mixture was stirred for 4 hours, after which solid sodium bicarbonate (5 g) was added until the pH had risen to 7. The solvents were removed in vacuo and the reside partitioned between ethyl acetate (100 ml) and water (50 ml). The aqueous layer was extracted with ethyl acetate (2×50 ml), and the combined organic extracts washed with brine (50 ml), dried (MgSO4), filtered and concentrated to give the diacetonide (4) (1.89 g, 74%).

EXAMPLE 3

Acylamine (14) preparation

4-Dimethylaminopyridine (20 mg, 0.164 mmol) and 4-nitrobenzoyl chloride (9) (276 mg, 1.49 mmol) were added to a solution of bis-(2,2-dimethyl-1,3-dioxane-5-yl)-amine (4) (79 mg, 0.322 mmol) in pyridine (2.5 ml) and dichloromethane (5 ml). The mixture was stirred for 5 hours at 60° C. before being diluted with ethyl acetate (80 ml) and successively washed with saturated sodium bicarbonate solution (2×25 ml) and brine (25 ml). Drying over magnesium sulfate, concentration and purification by flash chromatography (hexane/ethyl acetate, 1.5:1) gave bis-N-(2,2-dimethyl-1,3-dioxane-5-yl)-p-nitrobenzamide (10) (91 mg, 72%) as colourless crystals; mp.: 211° C. (needles, from hexane/acetone); m/z (CI, $NH_3$) 337 (M+H+-acetone, 100%).

EXAMPLE 4

N-(2'-Chloroethyl)-bis(1,3-O-isopropylidene-isopropyl)amine (40)

Method 1: To a solution of chloroacetaldehyde (45% w/w in $H_2O$, 278 mg, 1.59 mmol, 2 eq.) in dichloroethane (2 ml) was added diacetonide (4)(195 mg, 0.796 mmol) and NaBH$(OAc)_3$ (253 mg, 1.194 mmol, 1.5 eq.). After 1 h, NaOH solution (1 M, 2 ml) was added and the reaction mixture extracted with $Et_2O$ (60 ml). The organic layer was washed with brine (20 ml), dried (MgSO$_4$) and the residue was purified by flash chromatography (hexane:EtOAc, 4:1) to yield chloride (40) (136 mg, 55%) as a clear oil. Further elution of the column with EtOAc, then EtOAc MeOH, 9:1, yielded 54 mg diacetonide (4), to give 77% chloride (40) based on recovered starting material.

Method 2: To a solution of alcohol (42) (217 mg, 0.75 mmol) and DMAP (10 mg, cat.) in pyridine (1 ml) cooled to 0° C., was added methanesulphonyl chloride (116 $\mu$l, 1.50 mmol, 2 eq.). After warming to RT over 30 mins, tlc (EtOAc:hexane, 2:1) showed conversion of the alcohol ($R_f$ 0.3) to two products ($R_f$ 0.6 and 0.8), and only one ($R_f$ 0.8) after 16 h. The solvent was removed and the residue partitioned between $CH_2Cl_2$ (60 ml) and water (20 ml). The organic layer was washed with brine (20 ml), dried ($MgSO_4$) and concentrated. The residue was purified by flash chromatography (hexane:EtOAc, 4:1) to yield chloride (40) (116 mg, 49%) as a clear oil. MS (APCI+) m/z: 308/310 $(M+H)^+$ 70/30%, 250/252 $(M+H-Me_2CO)^+$ 100/35%; HRMS: $MH^+$ $C_{14}H_{27}NClO_4$ req. 308.1629; calc. 308.1630.

EXAMPLE 5

N-(2'-Azidoethyl)-bis(1,3-O-isopropylidene-isopropyl)amine (41)

Method 1: Sodium azide (41 mg, 0.624 mmol, 2 eq.) was added to a solution of chloride (40) (96 mg, 0.312 mmol) in DMF (1 ml). The reaction mixture was stirred at 60° C. for 18 h, by which time tlc (hexane:EtOAc, 2:1) showed a single product ($R_f$ 0.7). The solvent was removed and the residue was preadsorbed onto silica and purified by flash chromatography (hexane:EtOAc, 3:1) to yield azide (41) (87 mg, 89%) as a clear oil.

Method 2: To a solution of alcohol (42) (214 mg, 0.739 mmol) in DMF (2 ml) was added diphenylphosphoryl azide (319 $\mu$l, 1.48 mmol, 2 eq.) and DBU (221 $\mu$l, 2 eq.) After 30 mins, tlc (EtOAc:hexane, 2:1) showed some conversion of the alcohol ($R_f$ 0.3) to a major ($R_f$ 0.6) and a minor ($R_f$ 0.7) product, and after heating for 5 h at 60° C. only a single product ($R_f$ 0.7) and a trace of starting material. The solvent was removed and the residue partitioned between EtOAc (50 ml) and water (10 ml). The organic layer was washed with brine (20 ml), dried ($MgSO_4$) and concentrated. The residue was purified by flash chromatography (hexane:EtOAc, 3:1) to yield azide (41) (75 mg, 75%) as a clear oil. MS (APCI+) m/z: 315 $(M+H)^+$ 30%, 257 $(M+H-Me_2CO)^+$ 100%.

EXAMPLE 6

N,N-Bis(1,3-O-isopropylidene-isoprotyl)-1',2'-diaminoethane (39)

Method 1: Azide (41) (169 mg, 0.538 mmol) was dissolved in EtOAc (1 ml). Pd black (10 mg, cat.) was added and the reaction vessel was evacuated and filled with hydrogen. After stirring for 16 h, the reaction mixture was filtered through Celite and concentrated to give diamine 3 (155 mg, quant.) as a clear oil. MS (APCI+) m/z: 289 $(M+H)^+$ 100%, 231 $(M+H-Me_2CO)^+$ 20%; HRMS: $MH^+$ $C_{14}H_{29}N_2O_4$ req. 289.2127; calc. 289.2125.

Method 2: A solution of the Z-diamine (43) (580 mg, 1.4 mmol) in ethanol (6 ml) plus palladium black (80 mg) was hydrogenated at r.t. and pressure for 19 hours. T.l.c. analysis (ethyl acetate/ hexane, 1:1) indicated the appearance of some baseline product and no starting material ($R_f$ 0.43). The reaction mixture was filtered through a small pad of Celite eluting with ethyl acetate. The solvent was removed from the filtrate in vacuo to afford (39) as a colourless oil (395 mg, 100%).

EXAMPLE 7

N-(Methoxycarbonylmethyl)-bis (1,3-O-isopropylidene-isopropyl)amine (15)

To a solution of diacetonide (4) (244 mg, 0.995 mmol) in toluene (2 ml) was added methyl bromoacetate (282 $\mu$l, 2.98 mmol, 3 eq.), $EtN^iPr_2$ (340 $\mu$l, 1.99 mmol, 2 eq.) and $Bu_4NI$ (20 mg, cat.). The reaction mixture was refluxed for 15 h, by which time tlc (EtOAc:hexane, 1:1) showed complete conversion to the product ($R_f$ 0.5). The reaction mixture was cooled, diluted with EtOAc (50 ml), and washed with water (20 ml). The aqueous layer was extracted with EtOAc (50 ml) and the combined organic layers were washed with brine (20 ml), dried ($MgSO_4$) and concentrated. The brown oily residue was purified by flash chromatography (hexane:EtOAc, 3:1) to yield ester (5) (266 mg, 84%) as a clear oil. MS (APCI+) m/z: 318 $(M+H)^+$ 25%, 260 $(M+H-Me_2CO)^+$ 100%; HRMS: $MH^+$ $C_{15}H_{28}NO_6$ req. 318.1921; calc. 318.1917.

EXAMPLE 8

N-(2'-Hydroxyethyl)-bis(1,3-O-isopropylidene-isopropyl)amine (42)

To a solution of ester (5) (589 mg, 1.86 mmol) in THF (5 ml) cooled to 0° C. was added a solution of $LiBH_4$ in THF (~2.0 M, 2.79 ml, 3 eq.). After stirring at RT for 21 h, tic (EtOAc:hexane, 2:1) showed complete conversion of the ester ($R_f$ 0.7) to the alcohol ($R_f$ 0.3–0.4). The reaction was quenched with saturated $NH_4Cl$ solution (5 ml), and extracted with EtOAc (100 ml). The organic layer was washed with water (30 ml), brine (30 ml), dried ($MgSO_4$) and concentrated. The residue was purified by flash chromatography (EtOAc:hexane, 2:1 then 3:1) to yield alcohol (42) (473 mg, 88%) as a clear oil. MS (APCI+) m/z: 290 $(M+H)^+$ 40%, 272 $(M+H-H_2O)^+$ 20%, 232 $(M+H-Me_2CO)^+$ 100%; HPMS: $MH^+$ $C_{14}H_{28}NO_5$ req. 290.1967; calc. 290.1967.

EXAMPLE 9

N-Allyl-bis(1,3-O-isopropylidene-isopropyl)amine (9)

To a solution of diacetonide (4) (196 mg, 0.800 mmol) in DMF (1 ml) was added $K_2CO_3$ (221 mg, 1.60 mmol, 2 eq.) and allyl iodide (146 $\mu$l, 1.60 mmol, 2 eq.). The reaction mixture was heated at 70° C. for 6 h, by which time tlc (EtOAc:hexane, 2:1) showed complete conversion to the product ($R_f$ 0.8). The solvent was removed and the residue was partitioned between EtOAc (80 ml) and water (20 ml). The organic layer was washed with brine (20 ml), dried ($MgSO_4$) and concentrated. The residue was purified by flash chromatography (hexane:EtOAc, 4:1) to yield alkene (9) (198 mg, 87%) as a clear oil. MS (APCI+) m/z: 286 $(M+H)^+$ 60%, 228 $(M+H-Me_2CO)^+$ 100%.

EXAMPLE 10

N-(3'-Hydroxypropyl)-bis(1,3-O-isopropylidene-isopropyl)amine (10)

Alkene (9) (1.46 g, 5.12 mmol) was dissolved in tetrahydrofuran (5 ml) and a solution of 9-BBN (0.5 M in THF, 20.5 ml, 10.23 mmol, 2 eq.) was added. After stirring for 18 h, water (10 ml) was added, the reaction mixture was cooled to 0° C. and NaOH solution (1 M, 12 ml) and $H_2O_2$ (30% v/v, 4.5 ml) were added. After stirring for 30 mins at RT, and for 30 mins at 60° C. tlc (EtOAc:hexane, 2:1) showed a single product ($R_f$ 0.2). The reaction mixture was extracted with EtOAc (100 ml, 50 ml) and the combined organic layers were washed with brine (50 ml), dried (MgSO$_4$) and concentrated. The residue was purified by flash chromatography (toluene:acetone, 3:1) to yield alcohol 11 (1.48 g, 95%) as a clear oil, which crystallised upon storage at low temperature. m.p. 44–45° C.; MS (APCI+) m/z: 304 (M+H)$^+$ 100%, 246 (M+H−Me$_2$CO)$^+$ 45%.

EXAMPLE 11

N-(3'-D-Toluenesulphoxypropyl)-bis(1,3-O-isopropylidene-isopropyl)amine (74)

To a solution of alcohol (10) (1.125 g, 3.71 mmol) in pyridine (10 ml) with 3 Å sieves (1 g) was added toluenesulphonic anhydride (1.57 g, 4.82 mmol, 1.3 eq.). The reaction mixture became orange, and after 3 h, tlc (EtOAc:hexane, 2:1) showed conversion of the starting material ($R_f$ 0.2) to a single product ($R_f$ 0.7). The reaction mixture was filtered through a Celite plug, washing with CH$_2$Cl$_2$ (100 ml). The organic layer was washed with saturated CuSO$_4$ solution (3×30 ml), water (30 ml), brine (30 ml), dried (MgSO$_4$) and concentrated to give tosylate (74) (1.48 g, 87%) as an orange oil, which was used without further purification. MS (APCI+) m/z: 458 (M+H)$^+$ 100%, 400 (M+H−Me$_2$CO)$^+$ 20%.

EXAMPLE 12

N-(3-Azidopropyl)-bis(1,3-O-isopropylidene-isoprodyl)amine (11)

Method 1: The crude tosylate (74) (1.48 g) was dissolved in DMF (6 ml) and sodium azide (315 mg, 4.84 mmol, 1.5 eq.) was added. The reaction mixture was stirred for 15 h at RT and 1 h at 60° C., at which point tlc (EtOAc:hexane, 2:1) showed a single product ($R_f$ 0.7). The reaction mixture was preadsorbed onto silica, and purified by flash chromatography (hexane:EtOAc, 4:1) to yield azide (11) (845 mg, 69% over two steps) as a clear oil.

Method 2: To a solution of alcohol (10) (336 mg, 1.107 mmol) in DMF (4 ml) was added diphenylphosphoryl azide (360 µl, 1.66 mmol, 1.5 eq.) and DBU (250 µl, 1.5 eq.) After 30 mins, tlc (EtOAc:hexane, 2:1) showed some conversion of the alcohol ($R_f$ 0.3) to a single product ($R_f$ 0.6), and after heating for 20 h at 60° C. a different product ($R_f$ 0.7) and some starting material. Further diphenylphosphoryl azide (120 µl, 0.55 mmol, 0.5 eq.) and DBU (83 µl, 0.5 eq.) was added and the reaction mixture stirred for a further 4 h. The solvent was removed and the residue dissolved in EtOAc (100 ml). The organic layer was washed with water (30 ml), brine (30 ml), dried (MgSO$_4$) and concentrated. The residue was purified by flash chromatography (hexane:EtOAc, 4:1) to yield azide (11) (238 mg, 65%) as a clear oil. MS (APCI+) m/z: 329 (M+H)$^+$ 75%, 271 (M+H−Me$_2$CO)$^+$ 100%; HRMS: MH$^+$ C$_{15}$H$_{29}$N$_4$O$_4$ req. 329.2189; calc. 329.2194.

EXAMPLE 13

N,N-Bis(1,3-O-isopropylidene-isopropyl)-1',3'-diaminopropane (12)

Azide 13 (162 mg, 0.493 mmol) was dissolved in EtOAc (2 ml). Pd black (10 mg, cat.) was added and the reaction vessel was evacuated and filled with hydrogen. After stirring for 18 h, the reaction mixture was filtered through Celite and concentrated to give diamine (12) (149 mg, quant.) as a clear oil. MS (APCI+) m/z: 303 (M+H)$^+$ 100%, 245 (M+H−Me$_2$CO)$^+$ 20%; HRMS: MH$^+$ C$_{15}$H$_{31}$N$_2$O$_4$ req. 303.2289; calc. 303.2284.

EXAMPLE 14

Benzene-1,3,5-dicarboxylic acid tris({2'-[bis(1",3"-O-isopropylidene-isopropyl)-amino]-ethyl}-amide) (112)

To a solution of diamine 3 (155 mg, 0.537 mmol, 3.3 eq.) and EtN$^i$Pr$_2$ (92 µl, 3.3 eq.) in CH$_2$Cl$_2$ (5 ml) cooled to 0° C. was added 1,3,5-benzenetricarbonyl chloride (43 mg, 0.163 mmol, 1 eq.). After 20 mins, tlc (EtOAc:MeOH, 9:1) showed a major product ($R_f$ 0.7) which was UV active. After 3 h, the reaction mixture was diluted with CH$_2$Cl$_2$ (50 ml), and washed with water (10 ml), brine (10 ml) and dried (MgSO$_4$). The residue was purified by flash chromatography (toluene:acetone, 3:1, then 2:1, 3:2) to yield triamide dendrimer (112) (126 mg, 73%) as a clear oil. MS (APCI−) M/z: 1056 (M+Cl)$^-$ 100%; HRMS: MH$^+$ C$_{51}$H$_{85}$N$_6$O$_{15}$ req. 1021.6073; calc. 1021.6066.

EXAMPLE 15

Benzene-1,3,5-tricarboxylic acid tris({2'-[bis(1",3"-dihydroxy-isopropyl)-amino]-ethyl}-amide) (72)

Triamide (112) (16 mg, 0.016 mmol) was dissolved in TFA:H$_2$O (1:1), stirred for 16 h and the solvent was removed to give triamide dendrimer (72) (12 mg, quant.) as an oil. $δ_H$ (400 MHz, D$_2$O) 3.73–3.91 (42H, m, 3NHCH$_2$CH$_2$N(CH)$_2$, 12OCH$_2$), 8.24 (3H, s, 3ArH); $δ_C$ (50 MHz, D$_2$O) 35.7 (NHCH$_2$), 40.4 (NCH$_2$), 56.6 (CH), 64.4 (OCH$_2$), 129.6 (ArCH), 134.3 (ArC), 170.1 (C=O).

EXAMPLE 16

N,N,N-tris{3-[bis(1',3'-O-isopropylidene-isopropyl)-amino]-propyl}amine (75)

To a solution of diamine (12) (116 mg, 0.383 mmol, 1 eq.) and EtN$^i$Pr$_2$ (197 µl, 1.149 mmol, 3 eq.) in DMF (3 ml) was added tosylate (74) (398 mg, 0.870 mmol, 2.3 eq.). The reaction mixture was stirred at RT for 3 h, and at 80° C. for 16 h, by which time tlc (EtOAc:MeOH, 9:1) showed the formation of a major product ($R_f$ 0.1). The solvent was removed, and the residue preadsorbed onto silica prior to purification by flash chromatography (EtOAc, then EtOAc:MeOH, 19:1, then 9:1, 5:1) to yield amine dendrimer (75) (124 mg, 37%) as a clear oil. MS (APCI+) m/z: 874 (M+H)$^+$ 100%; HRMS:MH$^+$ C$_{45}$H$_{85}$N$_4$O$_{12}$ req. 873.6164; calc. 873.6149.

EXAMPLE 17

N,N,N-tris{3-[bis(1',3'-dihydroxy-isopropyl)-amino]-propyl}amine (76)

Amino dendrimer (75) (20 mg, 0.023 mmol) was dissolved in TFA:H$_2$O (1:1), stirred for 16 h and the solvent was removed to give the trifluoroacetate salt. $δ_H$ (400 MHz, D$_2$O) 2.17 (6H, m, 3CH$_2$CH$_2$CH$_2$), 3.23(6H, t, J 7.9, N(CH$_2$)$_3$), 3.48 (6H, t, J 7.8, 3CH$_2$NCH), 3.74 (6H, m, 6NCH), 3.83 (24H, m, 12OCH$_2$). The residue was dissolved in water and applied to an ion-exchange column (Amberlite, IR120, H$^+$), which was eluted first with water, and then ammonia solution (1N). The basic washings were concentrated to give amine dendrimer (76) (12 mg, 83%) as a white solid. MS (APCI+) m/z: 633 (M+H)$^+$ 100%.

EXAMPLE 18

Bis[1,3-di-(tert-butyloxycarbonylethoxy)-isopropyl]amine (77)

To a solution of (3) (615 mg, 3.72 mmol) in NaOH solution (50%, 5 ml) was added t-butyl acrylate (4.32 ml, 29.8 mmol, 8 eq.) and $Bu_4NHSO_4$ (253 mg, 0.745 mmol, 0.2 eq.). After stirring for 16 h, the reaction mixture was diluted with water (50 ml) and extracted with EtOAc (3×50 ml). The combined organic layers were washed with brine (50 ml) and dried ($MgSO_4$). The residue was purified by flash chromatography (EtOAc:hexane, 1:1, then 2:1) to yield tetraester (77) (820 mg, 33%) as a clear oil. MS (APCI+) m/z: 678 $(M+H)^+$ 100%.

EXAMPLE 19

Bis{1,3-di-[2'-bis(1'',3''-O-isopropylidene-isopropyl)-aminoethyl-aminocarbonyl-ethoxy]-isopropyl}amine (79)

Tetraester (77) (50 mg, 0.0737 mmol) was dissolved in $CH_2Cl_2$ (1 ml) and TFA (1 ml) and stirred for 24 h. The solvents were removed to give tetraacid (78): $\delta_H$ (200 MHz, $D_2O$) 2.43 (8H, t, J 5.9, $4CH_2CO_2H$), 3.47–3.59 (18H, m, 2NCH, $4OCH_2OCH_2$). To a solution of crude tetraacid (78) in DMF (0.5 ml) was added $EtN^iPr_2$ (77 µl, 0.442 mmol, 6 eq.), a solution of diamine (39) (131 mg, 6 eq.) in DMF (1 ml), and TBTU (189 mg, 0.590 mmol, 8 eq.). The reaction mixture was stirred for 22 h, and the solvent removed. The residue was partitioned between $Et_2O$ (50 ml) and water (20 ml) and the aqueous layer was extracted with $CH_2Cl_2$ (2×40 ml). The combined organic layers were dried ($MgSO_4$), and the residue was dissolved in $CH_2Cl_2$ and applied to a column packed with Sephadex LH20. Elution with $CH_2Cl_2$ yielded wedge (79) (90 mg, 80%) as a pale brown oil. MS (ES+) m/z: 1534.8 $(M+H)^+$ 10%, 767.9 $(M+2H)^{2+}$ 100%.

EXAMPLE 20

N-(2'-Azidoethyl)-bis[1,3-di-(tert-butyloxycarbonylethoxy)-isopropyl]amine (82)

To a solution of tetraester (77) (1.18 g, 1.75 mmol) in dichloroethane (15 ml) was added chloroacetaldehyde (45% w/w in $H_2O$, 458 mg, 2.62 mmol, 1.5 eq.) and $NaBH(OAc)_3$ (408 mg, 1.92 mmol, 1.2 eq.). After 40 mins, tlc (EtOAc:hexane, 2:1) showed the formation of a major product ($R_f$ 0.9), and some remaining starting material ($R_f$ 0.3). NaOH solution (1 M, 5 ml) was added and the reaction mixture extracted with EtOAc (150 ml). The organic layer was washed with brine (50 ml), dried ($MgSO_4$) and the residue concentrated to yield 1.28 g clear oil. Sodium azide (227 mg, 3.50 mmol, 2 eq.) was added to the solution of crude chloride in DMF (5 ml). The reaction mixture was stirred at 90° C. for 1.5 h, and the solvent was removed. The residue was dissolved in EtOAc (100 ml) and washed with water (30 ml). The aqueous layer was re-extracted with EtOAc (50 ml), and the combined organic layers were washed with brine (50 ml), and dried ($MgSO_4$). The residue was purified by flash chromatography (hexane:EtOAc, 5:1, then 4:1, 3:1) to yield azide (82) (700 mg, 54%) as a clear oil. Further elution of the column with EtOAc yielded 316 mg amine 3, to give 73% yield of azide based on recovered starting material. MS (APCI+) m/z: 747 $(M+H)^+$ 100%.

EXAMPLE 21

N-(2-Azidoethyl)-bis{1,',3'-di-[2''-bis(1''',3'''-O-isopropylidene-isopropyl)-aminoethyl-aminocarbonyl-ethoxy]-isopropyl}amine (83)

C2 azidotetraester (82) (204 mg, 0.273 mmol) was dissolved in $CH_2Cl_2$ (1 ml) and TFA (1 ml) and stirred for 20 h, at which point tlc (EtOAc:MeOH, 9:1) showed a single product ($R_f$ 0.3), and the solvents were removed. To a solution of crude tetraacid (80) in DMF (5 ml) was added $EtN^iPr_2$ (285 µl, 1.64 mmol, 6 eq.), a solution of diamine (39) (450 mg, 1.56 mmol, 5.7 eq.) in DMF (2 ml), and TBTU (526 mg, 1.64 mmol, 6 eq.). The reaction mixture was stirred for 17 h, and the solvent removed. The residue was dissolved in $CH_2Cl_2$ (100 ml) and washed with water (30 ml). The aqueous layer was re-extracted with $CH_2Cl_2$ (30 ml) and the combined organic layers were washed with brine (30 ml), dried ($MgSO_4$), and concentrated. The residue was dissolved in $CH_2Cl_2$ and applied to a column packed with Sephadex LH20. Elution with $CH_2Cl_2$ yielded wedge (83) (309 mg, 74%) as a pale brown oil. MS (ES+) m/z: 1604.2 $(M+H)^+$ 20%, 802.5 $(M+2H)^{2+}$ 100%; HRMS: $MH^+$ $C_{76}H_{139}N_{12}O_{24}$ req. 1604.0025; calc.1603.9918.

EXAMPLE 22

N,N-bis[1,3-di-(tert-butyloxycarbonylethoxy)-isopropyl]-1',2'-diaminoethane (81)

C2 azidotetraester (82) (184 mg, 0.246 mmol) was dissolved in EtOAc (2 ml). Pd black (20 mg, cat.) was added and the reaction vessel was evacuated and filled with hydrogen. After stirring for 4 h, IR of the reaction mixture showed no azide peak, and the reaction mixture was filtered through Celite and concentrated to give diamine (81) (177 mg, quant.) as a clear oil. MS (APCI+) m/z: 721 $(M+H)^+$ 100%.

EXAMPLE 23

N-(2-Azidoethyl)-bis(1',3'-di-{2''-bis[1''',3'''-di-(tert-butyloxycarbonylethoxy)-isopropyl]aminoethyl-aminocarbonyl-ethoxy}-isopropyl)amine (84)

C2 azidotetraester (82) (31 mg, 0.0415 mmol) was dissolved in $CH_2Cl_2$ (1 ml) and TFA (1 ml) and stirred for 5 h, at which point tlc (EtOAc:MeOH, 9:1) showed a single product ($R_f$ 0.3), and the solvents were removed. To the crude tetraacid (80) was added a solution of diamine (81) (177 mg, 0.246 mmol, 6 eq.) in DMF (3 ml), $EtN^iPr_2$ (43 µl, 6 eq.), and TBTU (79 mg, 6 eq.). The reaction mixture was stirred for 40 h, diluted with $CH_2Cl_2$ (100 ml), and washed with water (30 ml) and brine (30 ml). The organic layer was dried ($MgSO_4$), and concentrated. The residue was dissolved in $CH_2Cl_2$ and applied to a column packed with Sephadex LH20. Elution with $CH_2Cl_2$ yielded wedge (84) (132 mg, 96%) as a pale brown oil. MS (MALDI) m/z: 3372 $(M+K)^+$ 35%, 3356 $(M+Na)^+$ 50%, 3334 $(M+H)^+$ 100%, 3307 $(M-N_2+H)$ 70%, 3277 $(M-C(CH_3)_3+H)^+$ 100%; (ES+) m/z: 1668.1 $(M+2H)^{2+}$ 20%, 1112.4 $(M+3H)^{3+}$ 100%.

EXAMPLE 24

4,6-Dichloro-2-bis-(2,2-dimethyl-[1,3]dioxan-5-yl)-amino-1,3,5-triazine (113)

To a solution of 2,4,6-trichloro-1,3,5-triazine (500 mg, 2.7 mmol) in dry toluene (12 ml) were added DIPEA (472 µl) and a solution of bis-(2,2-dimethyl-[1,3]dioxan-5-yl)-amine 2 (664 mg, 2.7 mmol) in toluene (6 ml). The reaction mixture was heated at reflux with stirring for 50 minutes under argon. T.l.c. (ethyl acetate/hexane, 1:3) showed complete consumption of starting material ($R_f$ 0.03) and formation of a single product ($R_f$ 0.19). The reaction mixture was concentrated in vacuo and the residue dissolved in ethyl acetate, preadsorbed onto silica gel and purified by flash column chromatography (ethyl acetate/hexane, 1:3) to afford the title compound as a yellow solid (1025 mg, 96%). m.p. 127–130° C. (toluene). HRMS (CI+): Found 393.1096; $C_{15}H_{23}N_4O_4Cl_2$ requires 393.1088.

EXAMPLE 25

2-Chloro-4,6-bis[bis-(2,2-dimethyl-[1,3]dioxan-5-yl)-amino]-1,3,5-triazine (115)

To a solution of 4,6-dichloro-2-bis-(2,2-dimethyl-[1,3]dioxan-5-yl)-amino-1,3,5-triazine (113) (221 mg, 0.56 mmol) in dry toluene (1 ml) were added DIPEA (98 μl, 0.56 mmol) and a solution of bis-(2,2-dimethyl-[1,3]dioxan-5-yl)-amine (4) (140 mg, 0.56 mmol) in toluene (1 ml). The reaction mixture was heated at reflux with stirring for 50 hours under argon. T.l.c. (ethyl acetate/hexane, 1:2) indicated formation of a single product ($R_f$ 0.27) and a trace of starting material ($R_f$ 0.50). The reaction mixture was concentrated in vacuo and the residue dissolved in ethyl acetate, preadsorbed onto silica gel and purified by flash column chromatography (ethyl acetate/hexane, 1:3) to afford (115) as a yellow solid (109 mg, 53% over recovered starting material). m.p. 133–135° C. (toluene). m/z (APCI+): 602 (M+H+, 17%), 544 (M+H+−58, 100%). HRMS (CI+): Found 602.2957; $C_{27}H_{45}N_5O_8Cl$ requires 602.2940.

EXAMPLE 26

2,4-Bis[bis-(2,2-dimethyl-[1,3]dioxan-5-yl)-amino], 6-[dodecylamino]-1,3,5-triazine (116)

To a solution of the monochloro triazine 115 (54 mg, 0.10 mmol) in dry toluene (1 ml) was added a solution of dodecylamine (68 mg, 0.40 mmol) in toluene (1 ml). The reaction mixture was heated at reflux with stirring for 16 hours under argon. T.l.c. (ethyl acetate/hexane, 1:2) indicated formation of a single product ($R_f$ 0.27) and complete consumption of starting material ($R_f$ 0.41). The reaction mixture was concentrated in vacuo and the residue dissolved in ethyl acetate, preadsorbed onto silica gel and purified by flash column chromatography (ethyl acetate/hexane, 1:3) to afford (116) as a yellow oil (54 mg, 76%). m/z (APCI+):752 (M+H+, 100%), 694 (M+H+−58, 25%). HRMS (CI+): Found 751.5333; $C_{39}H_{71}N_6O_8$ requires 751.5335.

EXAMPLE 27

2,4-Bis[hexylamino],6-[bis-(2,2-dimethyl-[1,3]dioxan-5-yl)-amino]-1,3,5-triazine (114)

To a solution of the dichloro triazine (113) (141 mg, 0.36 mmol) in dry toluene (1 ml) was added a solution of nhexylamine (190 μl, 1.43 mmol) in toluene (2 ml). The reaction mixture was heated at reflux with stirring for 12 hours under argon. T.l.c. (ethyl acetate/hexane, 1:3) indicated formation of a single product ($R_f$ 0.19) and complete consumption of starting material ($R_f$ 0.34). The reaction mixture was concentrated in vacuo and the residue dissolved in ethyl acetate, preadsorbed onto silica gel and purified by flash column chromatography (ethyl acetate/hexane, 1:3) to afford (114) as a yellow oil (164 mg, 89%). HRMS (CI+): Found 523.3972; $C_{27}H_{51}N_6O_4$ requires 523.3972.

EXAMPLE 28

2,4-Bis[hexylamino],6- [bis-(1,3-dihydroxy-isopropyl)-amino]-1,3,5-triazine (67)

To the 2,4,6-trialkylamino triazine (114) (150 mg, 0.29 mmol) was added 70% aqueous acetic acid (3 ml) and the reaction mixture was stirred at room temperature for 13 hours. The reaction mixture was concentrated in vacuo and coevaporated with toluene (2×2 ml) to afford (67) as a white solid (126 mg, quantitative). m/z (APCI+): 443 (M+H+, 100% ), 425 (M+H+−18, 23%). HRMS (CI+): Found 443.3342; $C_{27}H_{51}N_6O_4$ requires 443.3347.

EXAMPLE 29

2-Benzyloxycarbonylaminoethanal (117)

This compound was prepared according to a modified literature procedure (Tetrahedron Lett. P184, 25, 5303). Under an atmosphere of argon, dry dichloromethane (30 ml) was added to powdered (3 Å) molecular sieves (2.13 g) which were previously dried for 2 hours. Solid pyridinium chlorochromate (5.50 g, 25.5 mmol) was then added and the mixture stirred at r.t. under argon for 10 minutes. A solution of 2-benzyloxycarbonylaminoethanol (prepared according to a literature procedure (Tetrahedron, 1991, 47, 2591)) (1.42 g, 7.28 mmol) in dry dichloromethane (30 ml) was added dropwise to the stirred mixture. After 2.5 hours t.l.c. (ethyl acetate/hexane 1:1) indicated complete conversion of the starting material ($R_f$ 0.26) to product ($R_f$ 0.61). The reaction mixture was diluted with diethyl ether (80 ml) and stirred for 10 minutes. The solution was then filtered through a silica plug, eluting with diethyl ether. The residual molecular sieves and pyridinium chlorochromate were collected and crushed in a mortar and pestle with diethyl ether and the resulting solution was filtered through the plug eluting with further diethyl ether. The resulting filtrate was concentrated in vacuo and the ensuing oil purified by flash column chromatography (ethyl acetate/hexane 1:1) to afford the title compound as a colourless oil (777 mg, 55%). $\delta_H$ (CDCl$_3$, 200 MHz): 4.16 (2H, d, J 5.0, CH$_2$CHO), 5.05 ※ 5.19 (3H, m, ArCH$_2$, NH), 7.30 ※ 7.48 (5H, m, ArH), 9.68 (1H, s, CHO).

EXAMPLE 30

Bis-(2,2-dimethyl-[1,3]dioxan-5-yl)-amino]-ethyl-carbamic acid benzyl ester (43)

The aldehyde (42) (472 mg, 2.4 mmol) was dissolved in dichloroethane (6 ml) and to this was added a solution of the amine (4) (628 mg, 2.6 mmol) in dichloroethane (4 ml) under an atmosphere of argon, followed by solid sodium triacetoxyborohydride (762 mg, 3.6 mmol) in one portion. The reaction mixture was stirred for 2 hours at r.t. after which time t.l.c. (ethyl-acetate/hexane, 1:1) indicated the appearance of a new product ($R_f$ 0.43) and a trace of starting material ($R_f$ 0.51). An aqueous solution of sodium hydroxide (1M, 20 ml) was added to the reaction mixture and stirred for a further 10 minutes. The reaction mixture was partitioned with ethyl acetate (100 ml) and the aqueous phase was extracted with further ethyl acetate (50 ml in two portions). The organic phases were combined and dried (MgSO$_4$), filtered and the filtrate concentrated in vacuo to give a residue which was purified by flash column chromatography (ethyl acetate/hexane, 1:1) to afford (43) as a yellow oil (821 mg, 81%). m/z (APCI+): 423 (M+H+, 100%), 365 (M+H+−58, 15%). HRMS (CI+): Found 423.2489; $C_{22}H_{35}N_2O_6$ requires 423.2496.

EXAMPLE 31

2-Chloro-4,6-bis(bis-(2,2-dimethyl-[1,3]dioxan-5-yl)-ethane-1,2-diamino)-1,3,5-triazine (69) and 2,4,6-tris(bis-(2,2-dimethyl-[1,3]dioxan-5-yl)-ethane-1,2-diamino)-1,3,5-triazine (70)

To a solution of 2,4,6-trichloro-1,3,5-triazine (66) (22 mg, 0.12 mmol) in dry toluene (2 ml) were added DIPEA (75 μl, 0.43 mmol) and a solution of the diamine (39) (120 mg, 0.43 mmol) in toluene (1.5 ml). The reaction mixture was heated at reflux with stirring for 16 hours under argon. T.l.c. (ethyl acetate/methanol, 19:1) showed formation of two products ($R_f$ 0.43, 0.51). The reaction mixture was concentrated in vacuo and the residue dissolved in ethyl acetate, preadsorbed onto silica gel and purified by flash column chromatography (ethyl acetate/methanol, 19:1) to afford the title compounds, both as yellow oils, the disubstituted triazine (69) (58 mg, 71%, eluted first), and the trisubstituted triazine (70) (33 mg, 29%, eluted second). Data for disubstituted triazine (69): m/z (APCI+): 963 (M+Na$^+$, 18%), 941 (M+H$^+$, 100%). HRMS (CI+): Found 940.6083; $C_{45}H_{82}N_9O_{12}$ requires 940.6077.

What is claimed:

1. A process for the preparation of a polymer which comprises carrying out polymerization using as a monomer, a branching agent or a chain termination agent, the compound represented by formula II

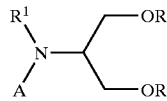

II wherein each R is hydrogen, a $C_{1-6}$ alkyl group, an alkylcarbonyl group or an aminocarbonyl group; or two R groups together represent a bridging group $C(R^2)_2$, wherein each $R^2$ is hydrogen, a $C_{1-6}$ alkyl group or an aryl group or two $R^2$ groups together represent oxygen;

wherein $R^1$ is hydrogen, a $C_{1-50}$ alkyl group optionally substituted by an amino, hydroxy, halo, alkoxy, oxo, aryl, heteroaryl, or carboxy group, or $R^1$ is an aminocarbonyl group, an alkylcarbonyl group, a monosaccharide optionally attached via a methylene or carbonyl group, an optionally protected 1,3-bishydroprop-2-yl group, a chlorocarbonyl group, or $R^1$ is $X(N(CH(CH_2OR)_2)_2)_n$, wherein X is a bond or a linking group containing 1 to 50 atoms in the backbone of the linking group, R is as defined above, and n is an integer of from 1 to 10;

wherein A is 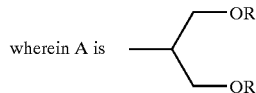

or $R^1$ and A taken together form a group -$(CR^4)_q$-, wherein q is 5 or 6, and each $R^4$, which may be the same or different, is hydrogen, a hydroxy group or $C_{1-4}$ alkyl group optionally substituted by a hydroxy or amino group, with the proviso that at least one $R^4$ is a hydroxy group;

or when $R^1$ is hydrogen, a hydroxy substituted $C_{1-6}$ alkyl group, or a $C_{2-5}$ acyl group, A is a 5- or 6-ring membered oxa or aza cycloalkyl group optionally attached via a $C_{1-2}$ alkylene group and substituted by one or more hydroxy or hydroxy $C_{1-4}$ alkyl groups;

with the proviso that when A is

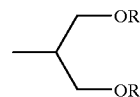

and each R is hydrogen, then $R^1$ is not $CH_2CH_2OH$.

2. The process of claim 1, wherein $R^1$ is a $C_{1-6}$ alkyl group optionally substituted by an amino, hydroxy, halo, alkoxy, oxo, aryl, heteroaryl, or carboxy group.

3. The process of claim 1, wherein n is an integer of 1, 2, 3, 4, 5 or 6.

4. A process for the preparation of a polymer which comprises carrying out polymerization using as a monomer, a branching agent or a chain termination agent, the compound represented by formula II

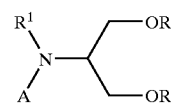

II wherein each R is hydrogen, a $C_{1-16}$ alkyl group, an alkylcarbonyl group or an aminocarbonyl group; or two R groups together represent a bridging group $C(R^2)_2$, wherein each $R^2$ is hydrogen, a $C_{1-6}$ alkyl group or an aryl group or two $R^2$ groups together represent oxygen;

wherein $R^1$ is hydrogen, a $C_{1-50}$ alkyl group optionally substituted by an amino, hydroxy, halo, alkoxy, oxo, aryl, heteroaryl, or carboxy group, or $R^1$ is an aminocarbonyl group, an alkylcarbonyl group, a monosaccharide optionally attached via a methylene or carbonyl group, an optionally protected 1, 3-bishydroprop-2-yl group, a chlorocarbonyl group, or $R^1$ is X(N(CH(CH_2OR)_2)_2)_n$, wherein X is a bond or a linking group containing 1 to 50 atoms in the backbone of the linking group, R is as defined above, and n is an integer of from 1 to 10;

wherein A is

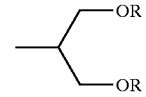

or $R^1$ and A taken together form a group - $(CR^4)_g$-, wherein q is 5 or 6, and each $R^4$, which may be the same or different, is hydrogen, a hydroxy group or $C_{1-4}$ alkyl group optionally substituted by a hydroxy or amino group, with the proviso that at least one $R^4$ is a hydroxy group;

or when $R^1$ is hydrogen, a hydroxy substituted $C_{1-6}$ alkyl group, or a $C_{2-5}$ acyl group, A is a 5- or 6-ring membered oxa or aza cycloalkyl group optionally attached via a $C_{1-2}$ alkylene group and substituted by one or more hydroxy or hydroxy $C_{1-4}$ alkyl groups;

with the proviso that when A is

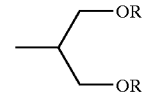

and each R is hydrogen, the $R^1$ is not $CH_2CH_2OH$, with the additional provisos that when A is

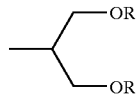

(a) when $R^1$ is hydrogen or an optionally protected 1, 3-bishydroxyprop-2-yl group, then at least two R groups are other than hydrogen; and
(b) when $R^1$ is hydrogen, and two R groups are hydrogen, the other two R groups are not methyl; and
(c) when X is 4-((1,3-bishydroxyprop-2-yl)amino)phenyl, then at least one R group is other than hydrogen; and
(d) when each R is hydrogen, $R^1$ is not $C(CH_3)_2CO_2H$ or $CH_2CO_2$.

5. The process of claim 4 wherein A is

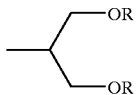

and $R^1$ is hydrogen, $CH_2COOCH_3$, $H_2NCH_2CO$, PhCO, $PhCH_2$ (where Ph is optionally substituted by $NO_2$, NCO or $NH_2$), ClCO, imidazolylcarbonyl, $HOOC(CH_2)_m$, $HO(CH_2)_m$, or $HOOC(CH_2)_mCO$, $H_2N(CH_2)_m$, where m is 1 to 50 or $R^1$ is 2-Phe-1, 3-bis-oxacyclohexane-5-yl, 1, 3-dihydroxyprop-2-yl or $X(N(CH(CH_2OR)_2)_2)_n$, where n is as defined above and X serves to link together two or more of the following groups

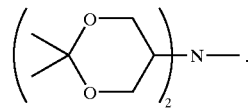

6. The process of claim 4, wherein said imidazolylcarbonyl is imidazol-1-ylcarbonyl.
7. The process of claim 4, wherein X serves to link 2, 3, 4, 5 or 6 of said groups.
8. The process of claim 4, wherein A is

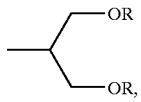

wherein each R is hydrogen, and $R^1$ is a $C_{1-20}$ alkyl group, an aminocarbonyl group of formula $R^{10}R^{11}NCO$ or an alkylcarbonyl group of formula $R^{11}CO$, wherein $R^{10}$ is hydrogen or $R^{11}$, and $R^{11}$ is a $C_{1-20}$ alkyl group.
9. The process of claim 4, wherein $R^1$ is a $C_6$—$C_{16}$ alkyl group.
10. The process of claim 4, wherein $R^1$ is a $C_8$—$C_{12}$ alkyl group.
11. The process of claim 4, wherein $R^{11}$ is a $C_{6-16}$ alkyl group.
12. The process of claim 4, wherein $R^{11}$ is a $C_8$—$C_{12}$ alkyl group.

13. The process of claim 4, wherein A is

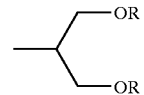

wherein each R is hydrogen or two R groups together represent a bridging group $C(R^2)_2$, wherein each $R^2$ is hydrogen, A $C_{1-6}$ alkyl group or an aryl group or both $R^2$ together represent oxygen, and wherein $R^1$ is an amino-substituted alkyl group.
14. The process of claim 4, wherein A and $R^1$ together form a group $-(CR^4)_q-$, wherein q is 5 or 6, and each $R^4$, which may be the same or different, is hydrogen, a hydroxy group or $C_{1-4}$ alkyl group optionally substituted by a hydroxy or amino group, with the proviso that at least one $R^4$ is a hydroxy group.
15. The process of claim 4, wherein $R^1$ is hydrogen, a hydroxy substituted $C_{1-16}$ alkyl group, or a $C_{2-5}$ acyl group, and A is a 5- or 6-ring membered oxa or aza cycloalkyl group optionally attached via a $C_{1-2}$ alkylene group and substituted by one or more hydroxy or hydroxy substituted $C_{1-4}$ alkyl groups.
16. A polymer comprising as a monomer, a branching agent or a chain termination agent, the compound represented by formula II

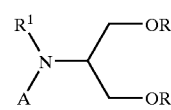

II wherein each R is hydrogen, a $C_{1-6}$ alkyl group, an alkylcarbonyl group or an aminocarbonyl group; or two R groups together represent a bridging group $C(R^2)_2$, wherein each $R^2$ is hydrogen, a $C_{1-6}$ alkyl group or an aryl group or two $R^2$ groups together represent oxygen;
wherein $R^1$ is hydrogen, a $C_{1-50}$ alkyl group optionally substituted by an amino, hydroxy, halo, alkoxy, oxo, aryl, heteroaryl, or carboxy group, or $R^1$ is an aminocarbonyl group, an alkylcarbonyl group, a monosaccharide optionally attached via a methylene or carbonyl group, an optionally protected 1, 3-bishydroprop-2-yl group, a chlorocarbonyl group, or $R^1$ is $X(N(CH(CH_2OR)_2)_2)_n$, wherein X is a bond or a linking group containing 1 to 50 atoms in the backbone of the linking group, R is as defined above, and n is an integer of from 1 to 10;
wherein A is

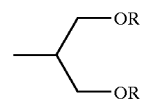

or $R^1$ and A taken together form a group $-(CR^4)_q-$, wherein q is 5 or 6, and each $R^4$, which may be the same or different, is hydrogen, a hydroxy group or $C_{1-4}$ alkyl group optionally substituted by a hydroxy or amino group, with the proviso that at least one $R^4$ is a hydroxy group;
or when $R^1$ is hydrogen, a hydroxy substituted $C_{1-6}$ alkyl group, or a $C_{2-5}$ acyl group, A is a 5or 6-ring member oxa or aza cycloalkyl group optionally attached via a $C_{1-2}$ alkylene group and substituted by one or more hydroxy or hydroxy $C_{1-4}$ alkyl groups;

with the proviso that when A is

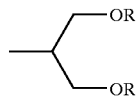

and each R is hydrogen, then $R^1$ is not $CH_2CH_2OH$, with the additional provisos that when A is

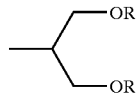

(a) when $R^1$ is hydrogen or an optionally protected 1, 3-bishydroxyprop-2-yl group, then at least two R groups are other than hydrogen; and
(b) when $R^1$ is hydrogen, and two R groups are hydrogen, the other two R groups are not methyl; and
(c) when X is 4-((1, 3-bishydroxyprop-2-yl) amino) phenyl, then at least one R group is other than hydrogen; and
(d) when each R is hydrogen, $R^1$ is not $C(CH_3)_2CO_2H$ or $CH_2CO_2H$.

17. The polymer of claim 16, wherein A is

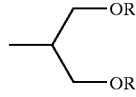

and $R^1$ is hydrogen, $CH_2COOCH_3$, $H_2NCH_2CO$, PhCO, $PhCH_2$ (where Ph is optionally substituted by $NO_2$, NCO or $NH_2$), ClCO, imidazolylcarbonyl, HOOC $(CH_2)_m$, $HO(CH_2)_m$, or $HOOC(CH_2)_mCO$, $H_2N(CH_2)_m$, where m is 1 to 50 or $R^1$ is 2-Phe-1, 3-bis-oxacyclohexane-5-yl, 1, 3-dihydroxyprop-2-yl or $X(N(CH(CH_2OR)_2)_2)_n$, where n is a defined above and X serves to link together two or more of the following groups

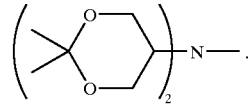

18. The polymer of claim 16, wherein said imidazolylcarbonyl is imidazol-1-ylcarbonyl.

19. The polymer of claim 16, wherein X serves to link 2, 3, 4, 5 or 6 of said groups.

20. The polymer of claim 16, wherein A is

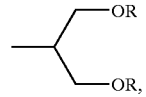

wherein each R is hydrogen, and $R^1$ is a $C_{1-20}$ alkyl group, an aminocarbonyl group of formula $R^{10}R^{11}NCO$ or an alkylcarbonyl group of formula $R^{11}CO$, wherein $R^{10}$ is hydrogen or $R^{11}$, and $R^{11}$ is a $C_{1-20\ alkyl\ group}$.

21. The polymer of claim 16, wherein $R^1$ is a $C_6$-$C_{16}$ alkyl group.

22. The polymer of claim 16, wherein $R^1$ is a $C_8$-$C_{12}$ alkyl group.

23. The polymer of claim 16, wherein $R^{11}$ is a $C_{6-16}$ alkyl group.

24. The polymer of claim 16, wherein $R^{11}$ is a $C_8C_{12}$ alkyl group.

25. The polymer of claim 16, wherein A is

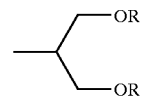

wherein each R is hydrogen or two R groups together represent a bridging group $C(R^2)_2$, wherein each $R^2$ is hydrogen, a $C_{1-6}$ alkyl group or an aryl group or both $R^2$ together represent oxygen, and wherein $R^1$ is an amino-substituted alkyl group.

26. The polymer of claim 16, wherein A and $R^1$ together form a group $-(CR^4)_q-$, wherein q is 5 or 6, and each $R^4$, which may be the same or different, is hydrogen, a hydroxy group or $C_{1-4}$ alkyl group optionally substituted by a hydroxy or amino group, with the proviso that at least one $R^4$ is a hydroxy group.

27. The polymer of claim 16, wherein $R^1$ is hydrogen, a hydroxy substituted $C_{1-6}$ alkyl group, or a $C_{2-5}$ acyl group, and A is a 5- or 6-ring membered oxa or aza cycloalkyl group optionally attached via a $C_{1-2}$ alkylene group and substituted by one or more hydroxy or hydroxy substituted $C_{1-4}$ alkyl groups.

* * * * *